United States Patent [19]

Burke et al.

[11] Patent Number: 5,663,064
[45] Date of Patent: Sep. 2, 1997

[54] RIBOZYMES WITH RNA PROTEIN BINDING SITE

[75] Inventors: John M. Burke, Burlington; Bruno Sargueil, Colchester, both of Vt.

[73] Assignee: University of Vermont, Burlington, Vt.

[21] Appl. No.: 371,986

[22] Filed: Jan. 13, 1995

[51] Int. Cl.[6] .......................... C12Q 1/68; C12N 15/85; C07H 21/04
[52] U.S. Cl. .................... 435/172.3; 435/6; 435/91.31; 435/172.1; 435/320.1; 435/325; 435/410; 536/23.1; 536/23.2; 536/24.5; 514/44
[58] Field of Search ................... 435/91.31, 320.1, 435/252.3, 240.1, 6, 172.1, 172.3, 240.2; 536/23.1, 23.2, 24.5; 514/44

[56] References Cited

U.S. PATENT DOCUMENTS

| | | | |
|---|---|---|---|
| 5,298,612 | 3/1994 | Jennings et al. | 536/23.2 |
| 5,459,015 | 10/1995 | Janjic et al. | 435/6 |
| 5,475,096 | 12/1995 | Gold et al. | 536/23.1 |

FOREIGN PATENT DOCUMENTS

| | | |
|---|---|---|
| 0360257 | 3/1990 | European Pat. Off. . |
| 0519463 | 12/1992 | European Pat. Off. . |
| 9103162 | 3/1991 | WIPO . |
| 9207065 | 4/1992 | WIPO . |
| 9315187 | 8/1993 | WIPO . |
| 9323569 | 11/1993 | WIPO . |
| 9402595 | 2/1994 | WIPO . |
| 9413791 | 6/1994 | WIPO . |
| 9521265 | 8/1995 | WIPO . |

OTHER PUBLICATIONS

Altman et al., *FASEB J.* 7:7 (1993).
Anderson et al., "Mutagenesis of the hairpin ribozyme," *Nucleic Acids Research* 22:1096–1100 (1994).
Bartel et al., "HIV–1 Rev Regulation Involves Recognition of Non–Watson–Crick Base Pairs in Viral RNA," *Cell* 67:529–536 (1991).
Bartel and Szostak, "Isolation of New Ribozymes From a Large Pool of Random Sequences," *Science* 261:1411–1418 (1993).
Beaudry and Joyce, "Directed Evolution of an RNA Enzyme," *Science* 257:635–641 (1992).
Bertrand and Rossi, *EBMO J.* 13:2904 (1994).
Berzal–Herranz et al., "Essential nucleotide sequences and secondary structure elements of the hairpin ribozyme," *EBMO J.* 12:2567–2574 (1993).
Berzal–Herranz et al., "In vitro selection of active hairpin ribozymes by sequential RNA–catalyzed clevage and ligation reactions," *Genes & Development* 6:129–134 (1992).
Buzayan et al., "Nucleotide sequence and newly formed phosphodiester bond of spontaneously ligated satellite tobacco ringspot virus RNA," *Nucleic Acids Research* 14:9729–9743 (1986).
Carter, "Adeno–Associated Virus Vectors," *Curr Opi. Biotech.* 3:533–539 (1992).

Cech, "Ribozymes and Their Medical Implications," *JAMA* 260:3030–3034 (1988).
Cech, "Ribozyme Engineering," *Current Opinion in Structural Biology* 2:605–609 (1992).
Chen et al., "Multitarget–Ribozyme Directed to Cleave at up to Nine Highly Conserved HIV–1 env RNA Regions Inhibits HIV–1 Replication–Potential Effectiveness Against Most Presently Sequenced HIV–1 Isolates," *Nucleic Acids Research* 20:4581–4589 (1992).
Chowrira et al., "Four Ribose 2'–Hydroxyl Groups Essential for Catalytic Function of the Hairpin Ribozyme," *J. Biol. Chem.* 268:19458–19462 (1993).
Chowrira et al., "In Vitro and in Vivo Comparison of Hammerhead, Hairpin, and Hepatitis Delta Virus Self–Processing Ribozyme Cassettes," *J. Biol. Chem.* 269:25856–25864 (1994).
Chowrira and Burke, "Binding and Cleavage of Nucleic Acids by the Hairpin Ribozyme," *Biochemistry* 30:8518 (1991) (from 208/154).
Chowrira et al., *Biochemistry* 32:1088 (1993).
Chowrira et al., *Nature* 354:320 (1991).
Chowrira and Burke, "Extensive Phosphorothioate Substitution Yields Highly Active and Nuclease–Resistant Hairpin Ribozymes," *Nucleic Acids Res.* 20:2835–2840 (1992).
Coetze et al., *Genes & Develop.* 8:1575 (1994).
Cohli et al., "Inhibition of HIV–1 Multiplication ini a Human CD4[+] Lymphocytic Cell Line Expressing Antisense and Sense RNA Molecules Containing HIV–1 Packaging Signal and Rev Response Element(s)," *Antisense Res. Dev.* 4:19–26 (1994).
Dropulic et al., "Functional Characterization of a U5 Ribozyme: Intracellular Suppression of Human Immunodeficiency Virus Type I Expression," *Journal of Virology* 66:1432–1441 (1992).
Elroy–Stein and Moss, "Cytoplasmic Expression System Based on Constitutive Synthesis of Bacteriophage T7 RNA Polymerase in Mammalian Cells," *Proc. Natl. Acad. Sci. USA* 87:6743–6747 (1990).
Feldstein et al., "Specific association between an endoribonucleolytic sequence from a satellite RNA and a substrate analogue containing a 2'–5'phosphodiester," *Proc. Natl. Acad. Sci. USA* 87:2623–2627 (1990).
Feldstein et al., "Two sequences participating in the autolytic processing of satellite tobacco ringspot virus complementary RNA," *Gene* 82:53–61 (1989).
Forster and Symons, "Self–Cleavage of Plus and Minus RNAs of a Virusoid and a Structural Model for the Active Sites," *Cell* 49:211–220 (1987).

(List continued on next page.)

*Primary Examiner*—John L. LeGuyader
*Attorney, Agent, or Firm*—Lyon & Lyon LLP

[57] ABSTRACT

Ribozyme having a ligand binding site formed as a double-stranded RNA and a single-stranded loop, the ribozyme having enzymatic activity to cleave and/or ligate itself or a separate RNA molecule.

15 Claims, 15 Drawing Sheets

OTHER PUBLICATIONS

Gao and Huang, "Cytoplasmic Expression of a Reporter Gene by Co-Delivery of T7 RNA Polymerase and T7 Promoter Sequence with Cationic Liposomes," *Nucleic Acids Res.* 21:2867–2872 (1993).

Guthrie, "Messenger RNA Splicing in Yeast: Clues to Why the Spliceosome Is a Ribonucleoprotein," *Science* 253:157–163 (1991).

Hampel et al., "The Hairpin Ribozyme," *Methods: A Companion to Methods in Enzymology* 5:37–42 (1993).

Hampel and Tritz, "RNA Catalytic Properties of the Minimum (–)sTRSV Sequence," *Biochemistry* 28:4929–4933 (1989).

Hampel et al., "Hairpin' Catalytic RNA Model: Evidence for Helices and Sequence Requirement for Substrate RNA," *Nucleic Acids Research* 18:299–304 (1990).

Haseloff and Gerlach, *Gene* 82:43 (1989).

Herschlag et al. *EBMO J.* 13:2913 (1994).

Herschlag and Cech, "Catalysis of RNA Cleavage by the *Tetrahymena thermophila* Ribozyme 1. Kinetic Description of the Reaction of an RNA Substrate Complementary to the Active Site," *Biochemistry* 29:10159–10171 (1990).

Jellinek et al., "Inhibitions of Receptor Binding by High–Affinity RNA Ligands to Vascular Endothelial Growth Factor," *Biochemistry* 33:10450–10456 (1994).

Jenison et al., "High Resolution Molecular Discrimination by RNA", *Science* 263:1425–1429 (1994).

Joseph et al., "Substrate selection rules for the hairpin ribozyme determined by in vitro selection, mutation, and analysis of mismatched substrates," *Genes & Development* 7:130–138 (1993).

Joyce, "Directed Molecular Evolution," *Scientific American* 267:90–97 (1992).

Kashani–Sabet et al., "Reversal of the Malignant Phenotype by an Anti–ras Ribozyme," *Antisense Research & Development* 2:3–15 (1992).

Kubik et al., "High–affinity RNA ligands to human α–thrombin," *Nucleic Acids Research* 22:2619–2626 (1994).

L'Huillier et al., "Cytoplasmic Delivery of Ribozymes Leads to Efficient Reduction in α–Lactalbumin mRNA Levels in C1271 Mouse," *Embo J.* 11:4411:4418 (1992).

Lieber et al., "Stable High–Level Gene Expression in Mammalian Cells by T7 Phage RNA Polymerase," *Methods Enzymol.* 217:47–66 (1993).

Lisziewicz et al., "Inhibition of Human Immunodeficiency Virus Type 1 Replication by Regulated Expression of a Polymeric Tat Activation Response RNA Decoy as a Strategy for Gene Therapy in AIDS," *Proc. Natl. Acad. Sci. U.S.A.* 90:8000–8004 (1993).

Milligan and Uhlenbeck, "Synthesis of Small RNAs Using T7 RNA Polymerase," *Methods Enzymol.* 180:51–62 (1989).

Mohr et al., "A tyrosyl–tRNA synthetase can function similarly to an RNA structure in the Tetrahymena ribozyme," *Nature* 370:147–150 (1994).

Noller, *Science* 256:1416 (1992).

Ohkawa et al., "Activities of HIV–RNA Targeted Ribozymes Transcribed From a 'Shot–Gun' Type Ribozyme–trimming Plasmid," *Nucleic Acids Symp. Ser.* 27:15–16 (1992).

Ojwang et al., "Inhibition of Human Immunodeficiency Virus Type 1 Expression by a Hairpin Ribozyme," *Proc. Natl. Acad. Sci. USA* 89:10802–10806 (1992).

Ortigao et al., "Antisense Effects of Oligodeoxynucleotides with Inverted Terminal Internucleotidic Linkages: A Minimal Modification Protecting Against Nucleoytic Degradation," *Antisense Research and Development* 2:129–146 (1992).

Perreault et al., "Mixed Deoxyribo–and Ribo–Oligonucleotides with Catalytic Activity," *Nature* 344:565–567 (1990).

Perrotta and Been, "Cleavage of Oligoribonucleotides by a Ribozyme Derived from the Hepatitis δ Virus RNA Sequence," *Biochemistry* 31:16–21 (1992).

Pieken et al., "Kinetic Characterization of Ribonuclease–Resistant 2'–Modified Hammerhead Ribozymes," *Science* 253:314–317 (1991).

Saldanha et al., *FASEB J.* 7:15 (1993).

Sarver et al., "Ribozymes as Potential Anti–HIV–1 Therapeutic Agents" *Science* 247:1222–1225 (1990).

Scanlon et al., "Ribozyme–Mediated Cleavage of c–fos mRNA Reduces Gene Expression of DNA Synthesis Enzymes and Metallothionein," *Proc. Natl. Acad. Sci. USA* 88:10591–10595 (1991).

Scaringe et al., "Chemical synthesis of biologically active oligoribonucleotides using β–cyanoethyl protected ribonucleoside phosphoramidites," *Nucl Acids Res.* 18:5433–5441 (1990).

Sullenger and Cech, *Science* 262:1566 (1993).

Szostak, "In Vitro Genes," *TIBS* 17:89–93 (1993).

Taira et al., "Construction of a novel RNA–transcript–trimming plasmid which can be used both in vitro in place of run–off and (G)–free transcriptions and in vivo as multi–sequences transcription vectors," *Nucleic Acids Research* 19:5125–5130 (1991).

Tsuchihaschi et al., *Science* 262:99–102 (1993).

Uhlenbeck, "A Small Catalytic Oligoribonucleotide," *Nature* 328:596–600 (1987).

Usman and Cedergren, "Exploiting the chemical synthesis of RNA," *TIBS* 17:334–339 (1992).

Usman et al., "Automated Chemical Synthesis of Long Oligoribonucleotides Using 2'–O–Silylated Ribonucleoside 3'–O–Phosphoramidites on a Controlled–Pore Glass Support: Synthesis of a 43–Nucleotide Sequence Similar to the 3'–Half Molecule of an *Escherichia coli* Formylmethoionine tRNA," *J. Am. Chem. Soc.* 109:7845–7854 (1987).

Ventura et al., "Activation of HIV–Specific Ribozyme Activity by Self–Cleavage," *Nucleic Acids Research* 21:3249–3255 (1993).

von Ashen and Schroeder, "RNA as a Catalyst: Natural and Designed Ribozymes," *BioEssays* 15:299–307 (1993).

Weerasinghe et al., "Resistance to Human Immunodeficiency Virus Type 1 (HIV–1) Infection in Human CD4+ Lymphocyte–Derived Cell Lines Conferred by Using Retroviral Vectors Expressing an HIV–1 RNA–Specific Ribozyme," *Journal of Virology* 65:5531–5534 (1994).

Wilhelm and Vale, "RNA on the Move: the mRNA Localization Pathway," *J. Cell. Biol.* 123:269–274 (1993).

Witherell et al., "Specific Interaction between RNA Phage Coat Proteins and RNA," *Prog. Nuc. Acid Res. Mol. Biol.* 40:185–220 (1991).

Woolf et al., "Specificity of Antisense Oligonucleotides in vivo," *Proc. Natl. Acad. Sci. USA* 89:7305–7309 (1992).

Yu et al., "A Hairpin Ribozyme Inhibits Expression of Diverse Strains of Human Immunodeficiency Virus Type 1," *Proc. Natl. Acad. Sci. USA* 90:6340–6344 (1993).

Zabner et al., "Adenovirus–Mediated Gene Transfer Transiently Corrects the Chloride Transport Defect in Nasal Epithelia of Patients with Cystic Fibrosis," *Cell* 75:207–216 (1993).

Zhou et al., "Synthesis of Functional mRNA in Mammalian Cells by Bacteriophage T3 RNA Polymerase," *Mol. Cell. Biol.* 10:4529–4537 (1990).

```
            A C              GAG
            C G            C      A
    C       U A            A      G
  U   A     G G            U      G
  C-G       G G            G      A
  U-A       U             A      A
  C-G       G G           A      C
  C-G     U   G           C      C
  G-CGU   C-G             U      C
  |   U   G-C             C-G
  A-UUA   A-U             G-C
  G   A   UG-C            U-A
  G-C   C  |              C-G
...G-C... UA-U            C-G
          G-C         A-U U  |
          A-U         G-U    A-U
         ..C-GG..     A-U   ...A-U...
                     ..G-CCC..
    L1      tat         70K    α-Sarcin U
                            C   U
   U C                      U   U
  A   G                     G-C
  A   U                     G-C
  C   A                     G-C
  U-A                       G-C
  A-U                       A-UCUC
  C-G       G U             |    G
  C-G      A   G            U-AAACC
  C-GU     C   C            C-G
  U   C    A-U              C-G           C A
  C-GU     A-U              U-A          G   A
  U-A      C-G              U-A          C-G
  C-GG     U-G              A-U          U-A
  A   A    CU-A             C-G          U-A
  C-G      G   C            G-C          U-A
  A-U      UC-G             A  A         G-C
  U-A      C-G              G  A         A-UUA
  U-A      U  |             C-GG         |  A
  G-U      U-A              A-U          G-CCCU
  G-C      U-A             ...G-C...     G-C
...AAC AUU... G-C                        A-U
         ..G-C...                        C-G
                                         G-C
                                         C-G
                                      ...GAC   UAG...

L4       IREP         p57            L10
```

FIG. 13.

FIG. 14a.
RBE1 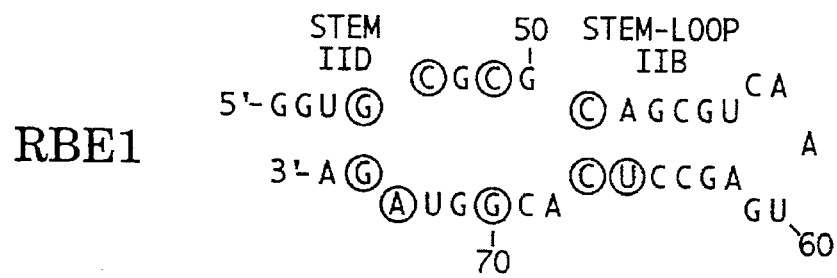
RBE2 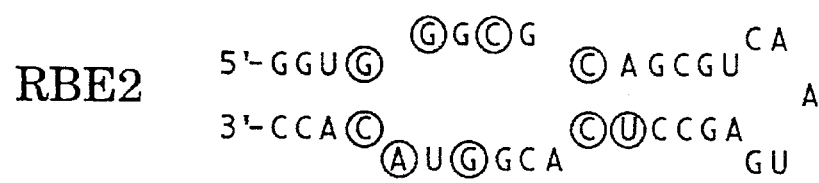
RBE3 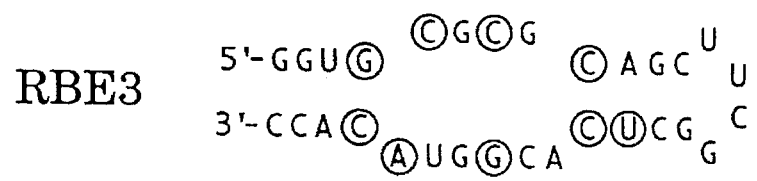
FIG. 14b.
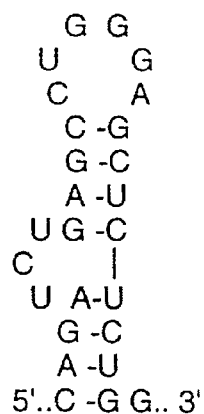

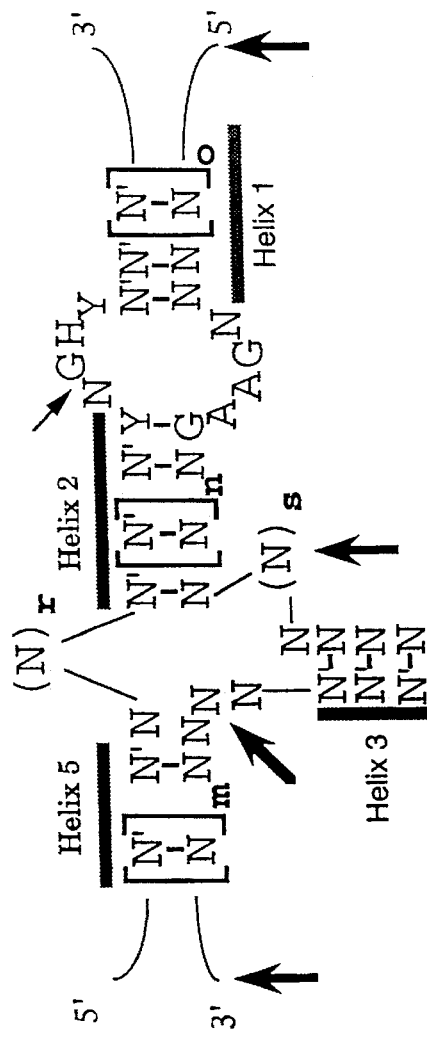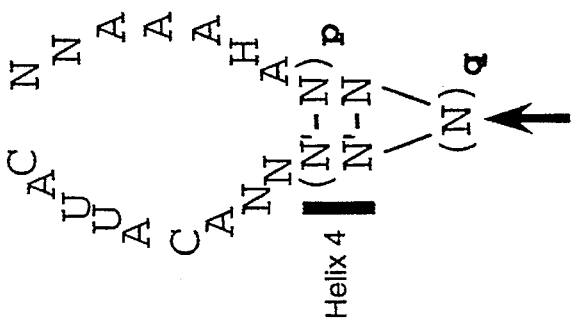
FIG. 18.

RIBOZYMES WITH RNA PROTEIN BINDING SITE

BACKGROUND OF THE INVENTION

This invention relates to ribozymes.

The following is a brief description of publications concerning ribozymes. None are admitted to be the prior art to the pending claims, and all are incorporated by reference herein.

The self-cleaving RNAs found in viruses and virusoids constitute a class of RNA catalysts, and their potential interactions with proteins in vivo remains largely unknown. These ribozymes can be converted into trans acting ribozymes that catalyze the site specific cleavage of an RNA substrate molecule (Hampel & Tritz, 1989 *Biochemistry* 28, 4929; Perrotta & Been, 1992 *Biochemistry* 31, 16; Uhlenbeck, 1987 *Nature* 328, 596).

Six basic varieties of naturally-occurring enzymatic RNAs are known presently. Each can catalyze the hydrolysis of RNA phosphodiester bonds in trans (and thus can cleave other RNA molecules) under physiological conditions. Table I summarizes some of the characteristics of these ribozymes. In general, enzymatic nucleic acids act by first binding to a target RNA. Such binding occurs through the target binding portion of a enzymatic nucleic acid which is held in close proximity to an enzymatic portion of the molecule that acts to cleave the target RNA. Thus, the enzymatic nucleic acid first recognizes and then binds a target RNA through complementary base-pairing, and once bound to the correct site, acts enzymatically to cut the target RNA. Strategic cleavage of such a target RNA will destroy its ability to direct synthesis of an encoded protein. After an enzymatic nucleic acid has bound and cleaved its RNA target, it is released from that RNA to search for another target and can repeatedly bind and cleave new targets.

The specificity of the ribozyme can be altered in a predictable manner without loss of catalytic efficiency, and for this reason, such ribozymes have considerable potential for inactivating gene expression through the cleavage of targeted RNA (Cech, 1988 *JAMA* 260, 3030). In vivo, a targeted ribozyme may encounter many obstacles, including the ability to find its cognate substrate, fold into a catalytically active conformation, resist cellular nucleases, be able to discriminate its target among other RNAs, and eventually turn over to repeat the process.

The enzymatic nature of a ribozyme is advantageous over other technologies, such as antisense technology (where a nucleic acid molecule generally simply binds to a nucleic acid target to block its translation) since the concentration of ribozyme necessary to affect a therapeutic treatment is lower than that of an antisense oligonucleotide. This advantage reflects the ability of the ribozyme to act enzymatically. Thus, a single ribozyme molecule is able to cleave many molecules of target RNA. In addition, the ribozyme is a highly specific inhibitor, with the specificity of inhibition depending not only on the base pairing mechanism of binding to the target RNA, but also on the mechanism of target RNA cleavage. Single mismatches, or base-substitutions, near the site of cleavage can completely eliminate catalytic activity of a ribozyme (Chowrira & Burke, 1991 *Biochemistry* 30, 8518; Joseph et al., 1993 *Genes & Develop.* 7, 30). Similar mismatches in antisense molecules do not prevent their action (Woolf et al., 1992 *Proc. Natl. Acad. Sci. USA*, 89, 7305-7309). Thus, the specificity of action of a ribozyme is greater than that of an antisense oligonucleotide binding the same RNA site.

The following publications generally discuss ribozymes, and in particular hairpin ribozymes. Van Tol et al., 1991 (*Virology* 180, 23) describe a hairpin ribozyme structure able to circularize. Hisamatsu et al., 1993 (*Nucleic Acids Symp. Ser.* 29, 173) describe hairpin ribozymes having a long substrate binding site in helix 1. Berzal-Herranz et al., 1993 (*EMBO J.* 12,2567) describe essential nucleotides in the hairpin ribozyme. Hampel and Tritz, 1989 (*Biochemistry* 28, 4929) describe a hairpin ribozyme derived from the minus strand of tobacco ringspot virus satellite [(−) sTRSV] RNA. Haseloff and Gerlach 1989 (*Gene* 82, 43) describe sequences required for self-cleavage reactions catalyzed by the (−) sTRSV RNA. Feldstein et al., 1989 (*Gene* 82, 53) tested various models of transcleaving motifs derived from (−) sTRSV RNAs. The hairpin ribozyme can be assembled in various combinations to catalyze a unimolecular, bimolecular or a trimolecular cleavage/ligation reaction (Berzal-Herranz et al., 1992, *Genes & Develop.* 6, 129; Chowrira and Burke, 1992 *Nucleic Acids Res.* 20, 2835; Komatsu et al., 1993 *Nucleic Acids Res.* 21, 185; Komatsu et al., 1994 *J. Am. Chem. Soc.* 116, 3692; Chowrira et al., 1994 *J. Biol. Chem.* 269, 25856). Increasing the length of helix 1 and helix 4 regions do not significantly affect the catalytic activity of the hairpin ribozyme (Hisamatsu et al., 1993 supra; Chowrira and Burke, 1992 supra; Anderson et al., 1994 *Nucleic Acids Res.* 22, 1096). For a review of various ribozyme motifs, and hairpin ribozyme in particular, see Burke, 1994 *Nucleic Acids & Mol. Biol.* 8, 105, eds. Eckstein and Lilley, Springer-Verlag, Germany; Ahsen and Schroeder, 1993 *Bioessays* 15, 299; Cech, 1992 *Curr. Opi. Struc. Bio.* 2, 605; and Hampel et al., 1993 *Methods: A Companion to Methods in Enzymology* 5, 37.

A hairpin ribozyme●substrate complex includes two intermolecular helices formed between the ribozyme and the target RNA (helix 1 and helix 2). The length of helix 1 can be varied substantially without affecting the catalytic activity of the ribozyme (Hisamatsu et al., 1993 supra). However, the length of helix 2 is reported to be sensitive to variation. The length of helix 2 is normally between 3 and 5 base-pairs long (Hampel & Tritz, 1989 supra; Feldstein et al. 1989 supra; Haseloff and Gerlach, 1989 supra, Hampel et al., 1990 supra; Feldstein et al., 1990 *Proc. Natl. Acad. Sci. USA* 87, 2623). Several reports suggest that mutations within this helix significantly inhibit ribozyme activity (Hampel et al., 1990 supra; Feldstein et al., 1990 supra; Chowrira & Burke, 1991 *Biochemistry* 30, 8518; Joseph et al., 1993 *Genes & Develop.* 7, 130). It is also believed in the art that the length of helix 2 should be between 3 and 5 bp (Hampel et al., 1988 EPO 360 257; Hampel et al., 1993 supra, Cech, 1992 supra; von Ahsen and Schroeder, 1993 supra; Hisamatsu et al., 1993 supra, Anderson et al., 1994 supra).

RNA-protein interactions are involved in many fundamental cellular processes. Well known examples of such ribonucleoproteins include RNase P, telomerase, Signal Recognition particles (SRP), the spliceosome, and the ribosome. Other examples of RNA-protein interactions occur during RNA processing and polyadenylation, and RNA trafficking within the cell.

It has been clearly demonstrated in the case of prokaryotic RNAse P and group I and II introns that the RNA is the catalytic component of the reaction. There is also accumulating evidence that 23S RNA of the ribosome (Noller et al., 1992 *Science* 256, 1416), and the snRNP RNAs (Guthrie, 1991 *Science* 253, 157) can at least partially catalyze translation and splicing, respectively. For the two latter examples, there is obviously an absolute requirement for many protein factors. At least 50 different proteins are involved in spliceosome assembly and function, up to 82 proteins in the ribosome, with many more required for translation. In the group I and group II introns, splicing is improved (in velocity and accuracy) by protein splicing factors (Coetze et al., 1994 *Genes & Develop.* 8, 1575; Mohr et al., 1994 *Nature* 370, 147; Saldanha et al., 1993 *FASEB. J.* 7, 15). Similarly, the protein component of RNase P is required for activity in vivo, and facilitates pre-tRNA cleavage in vitro (Altman et al., 1993 *FASEB. J* 7, 7). Thus, even if RNA is an efficient catalyst in vitro, in vivo RNA catalysis occurs in concert with proteins. Another important difference between in vitro and in vivo RNA catalysis is that RNA molecules are not homogeneously diffused throughout the cellular milieu. RNAs are dispatched in the cell by a still unknown protein machinery, and RNA-protein interactions are a key step in this mechanism (Wilhelm & Vale, 1993 *J. Cell. Biol.* 123, 269).

Jennings et al., U.S. Pat. No. 5,298,612 describe potential hammerhead ribozyme●protein interactions. It states:

Applicants have found that base-pairing in the group P is not required for cleavage of a target RNA. Accordingly, when nucleotide sequences X and Y are comprised solely of ribonucleotides and the group P is comprised solely of ribonucleotides, the ribonucleotides of group P may be base-paired for purpose other than to effect cleavage of a target RNA. Such purposes would include to allow the binding of cellular factors, such as RNA binding proteins or other cellular factors. Similarly, where the nucleotide sequences X and Y are comprised solely of deoxyribonucleotides, and the group P is comprised solely of deoxyribonucleotides, the deoxyribonucleotides of the group P may be base-paired for purposes other than involvement in endonuclease cleavage, such as interaction with DNA binding proteins or other cellular factors, which may, for example, effect cellular distribution of the endonuclease.

SUMMARY OF THE INVENTION

This invention concerns ribozymes having a double-stranded RNA and a single-stranded loop or single-stranded RNA-protein binding site incorporated into their structure. Binding of ligands (e.g., proteins) to these binding-sites preferably does not significantly affect the catalytic activity of the ribozyme, and may in fact improve the activity of the ribozyme. The site may be incorporated in a manner which does not significantly decrease the catalytic activity of the ribozyme. This site allows a protein to specifically bind to the ribozyme, and thereby potentially enhance activity and create a ribonucleoprotein that may be more efficiently targeted to a RNA substrate molecule.

By "ligand" is meant a macromolecule (e.g., peptide, protein, alkaloid, or lipid) that can contact a double-stranded RNA and a single-stranded loop or single-stranded RNA with high specificity and a high affinity.

Specifically, in one example, we show that the introduction of an R17 coat protein binding site in a hairpin ribozyme structure does not interfere with the enzyme activity, but actually improves its cleavage rate by 2-fold. The R17 coat-protein (R17cp) originates from the *E. coli* R17 RNA bacteriophage. It tightly binds to a 23 nucleotides hairpin RNA (R17bs), and functions both as a translational repressor and in the initiation of phage assembly (Witherell et al., 1991 *Prog. Nuc. Acid. Res. Mol. Biol.* 40, 185). We show that the increase in catalytic efficiency correlates with stabilization of the ribozyme tertiary structure. The R17 coat protein binds the modified ribozyme as efficiently as its native binding site, does not reduce catalysis, and remains associated with the ribozyme during catalysis. Therefore, a ribozyme can function efficiently in vitro as a ribonucleoprotein.

This invention thus features improved ribozymes, based on the hairpin motif described by Hampel et al., in Hampel and Tritz 28 *Biochemistry* 4929, 1989; Hampel et al., 18 *Nucleic Acid Res.* 299, 1990 and Hampel et al., EP 0360257, and on other ribozyme motifs (as above), such as the hammerhead motif.

The invention provides a method for producing a class of enzymatic cleaving agents which exhibit a high degree of specificity for the RNA of a desired target. The enzymatic nucleic acid molecule is preferably targeted to a highly conserved sequence region of a target-encoding mRNA such that specific treatment of a disease or condition can be provided with either one or several enzymatic nucleic acids. Such enzymatic nucleic acid molecules can be delivered exogenously to specific cells as required. Alternatively, the ribozymes can be expressed from DNA or RNA vectors that are delivered to specific cells.

By "vectors" is meant any nucleic acid- and/or viral-based technique used to deliver a desired nucleic acid.

The site-specific binding of a ligand can affect ribozyme catalysis in vitro, and can overcome some in vivo targeting obstacles. This is shown below in a model ribonucleoprotein system using the R17 *E. coli* phage coat protein and the hairpin ribozyme. Those in the art will recognize that this is a non-limiting example of the invention and that other RNA binding proteins can be associated with the desired ribozymes and cause targeting to the desired site in an animal or plant, and/or increase ribozyme activity. The RNA binding protein may be naturally occurring or may be introduced in vitro or in vivo to have the desired function.

The engineered ribonucleoproteins may be used to localize a ribozyme in vivo. Here we show that extending helix 4 of a hairpin ribozyme to bind a protein improves by two fold the rate of catalysis, A UV cross-linking assay indicates that the 2-fold enhancement correlates directly with a stabilization of the tertiary structure of the ribozyme's large internal loop (loop B). We show that protein binding does not alter $k_{cat}$ or $K_M$ of the reaction, and that the protein remains bound during catalysis. These studies indicate that ribozymes can be engineered to efficiently function as a ribonucleoprotein in vitro.

Thus in a first aspect, the invention features a ribozyme having an RNA-binding protein-binding site. For example, the protein binding site is a double-stranded RNA sequence and a loop. The protein binding site may be provided at helix 4 of a hairpin ribozyme, or in stem II of a hammerhead ribozyme, or stem IV of HDV ribozyme or at the 5' end or the 3' end of such ribozymes (see FIG. 5). It can also be provided in non essential or non-critical loops or helixes or termini of other ribozyme motifs.

By "ribozyme" is meant a RNA molecule (including those found with non-ribonucleotides at some positions see, below) having the general structure discussed in Table 1, and shown in FIGS. 1–5, where each N and N' is independently any desired base (with a dash representing hydrogen bonding between the bases). Those in the art in the art will recognize that 100% hydrogen bonding between each of these bases is not required, rather sufficient hydrogen bonding to form the necessary secondary structure in the form of helices is all that is needed for enzymatic activity. While the ribozymes shown in the figures have a free 5' end, that 5' end may be base-paired or covalently linked with the 3' end of the substrate if it is desired to have a self-cleaving activity. Alternately, the 5'-end of the substrate can be covalently linked with the 3' end of the ribozyme.

A number of ligands (e.g., proteins) have been identified that bind to specific RNA structural motifs (reviewed by Witherell et al., 1991 *Prog. Nucleic. Acids Res. Mol. Biol.* 40, 185). In non-limiting examples, FIGS. 12 through 17 show examples of RNA structural motifs that bind to specific ligands like proteins. These ligand-RNA interactions modulate a wide range of cellular processes like for example protein synthesis, viral packaging, RNA transport. Any RNA structural motif that specifically binds to a ligand can potentially be incorporated into the ribozyme structure, provided the catalytic activity of the ribozyme is not affected.

In a related aspect the invention features ribozymes having an associated RNA binding protein which is not naturally attached to the ribozyme, but is associated by bonding in a protein-nucleic acid interaction manner with a sequence on the ribozyme.

In another aspect the invention features a method for increasing activity of a ribozyme by increasing the length of a helix not necessary for complete ribozyme activity (e.g., helix 4 or a hairpin, Stem IV of HDV and stem II of a hammerhead) shown in FIGS. 1–5, and in particular, by increasing that length with a double-stranded RNA sequence to which a protein is able to bind, and to which a protein may be bound.

In addition, the method involves localizing a ribozyme by providing a protein binding sequence to which a localizing protein can be bound (for a review see Wilhelm and Dale, 1993 *J. Cell. Biol.* 123, 269).

In the most preferred embodiments, the protein binding sites shown in the figures herein are incorporated at least in part into a hairpin ribozyme motif of a structure shown in FIG. 18. Such introduction will allow binding to that ribozyme and either an enhanced or lowered enzymatic activity. Ligand binding to the ribozyme may also allow targeting of the ribozyme to various cellular sites or components.

Other features and advantages of the invention will be apparent from the following description of the preferred embodiments thereof, and from the claims.

DESCRIPTION OF PREFERRED EMBODIMENTS

The drawings will first briefly be described.

FIG. 1 is a diagrammatic representation of the hammerhead ribozyme domain (SEQ ID Nos. 1 and 2) known in the art. Stem II can be ≧2 base-pair long, or can even lack base pairs and consist of a loop region.

FIG. 2 A–C shows the secondary structure of a hairpin ribozyme (SEQ ID No. 3), the R 17 coat protein binding site (SEQ ID No. 4), and a hairpin ribozyme with the coat protein binding site (SEQ ID No. 5) respectively. Helix 2 and helix 3 may or may not be linked by one or more nucleotides (e.g., 5 Cytidines). 3'P refers to 3' cleavage product. Arrow indicates the cleavage/ligation site.

FIG. 3 is a diagrammatic representation of the general structure of a hairpin ribozyme (SEQ ID Nos. 6 and 7). Helix 2 (H2) is provided with a least 4 base pairs (i.e., n is 1, 2, 3 or 4) and helix 5 is optional and may be provided of length 2 or more bases (preferably 3–20 bases, i.e., m is from 1–20 or more). Helix 2 and helix 5 may be covalently linked by one or more bases (i.e., r is ≧1 base). Helix 1, 4 or 5 may also be extended by 2 or more base pairs (e.g., 4–20 base pairs) to stabilize the ribozyme structure, and preferably is a protein binding site. In each instance, each N and N' independently is any normal or modified base and each dash represents a potential base-pairing interaction. These nucleotides may be modified at the sugar, base or phosphate. Complete base-pairing is not required in the helices, but is preferred. Helix 1 and 4 can be of any size (i.e., o and p is each independently from 0 to any number, e.g., 20) as long as some base-pairing is maintained. Essential bases are shown as specific bases in the structure, but those in the art will recognize that one or more may be modified chemically (abasic, base, sugar and/or phosphate modifications) or replaced with another base without significant effect. Helix 4 can be formed from two separate molecules, i.e., without a connecting loop. The connecting loop when present may be a ribonucleotide with or without modifications to its base, sugar or phosphate. "q" is ≧2 bases. The connecting loop can also be replaced with a non-nucleotide linker molecule. H, refers to bases A, U or C. Y refers to pyrimidine bases. "_" refers to a covalent bond.

By "base-pair" is meant a nucleic acid that can form hydrogen bond(s) with other RNA sequence by either traditional Watson-Crick or other non-traditional types (for example Hoogsteen type) of interactions.

Figure 8:
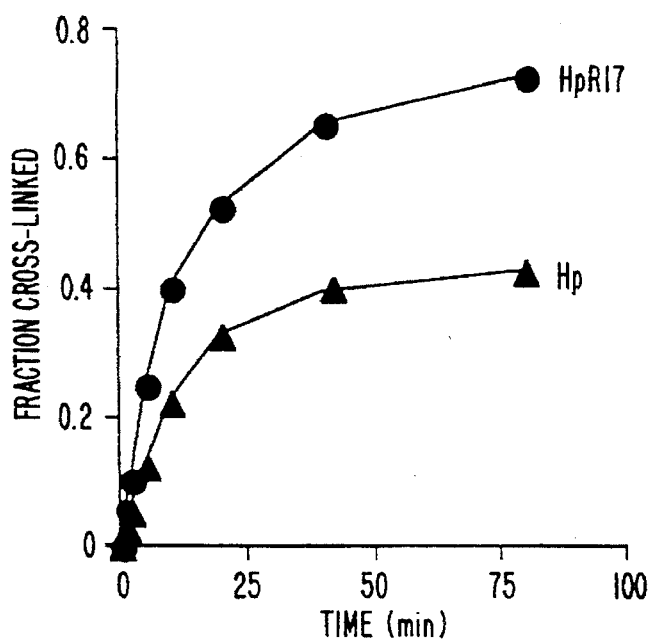

FIG. 8 Effect of R17 binding site on UV cross-linking by the hairpin ribozyme.

Figure 9:
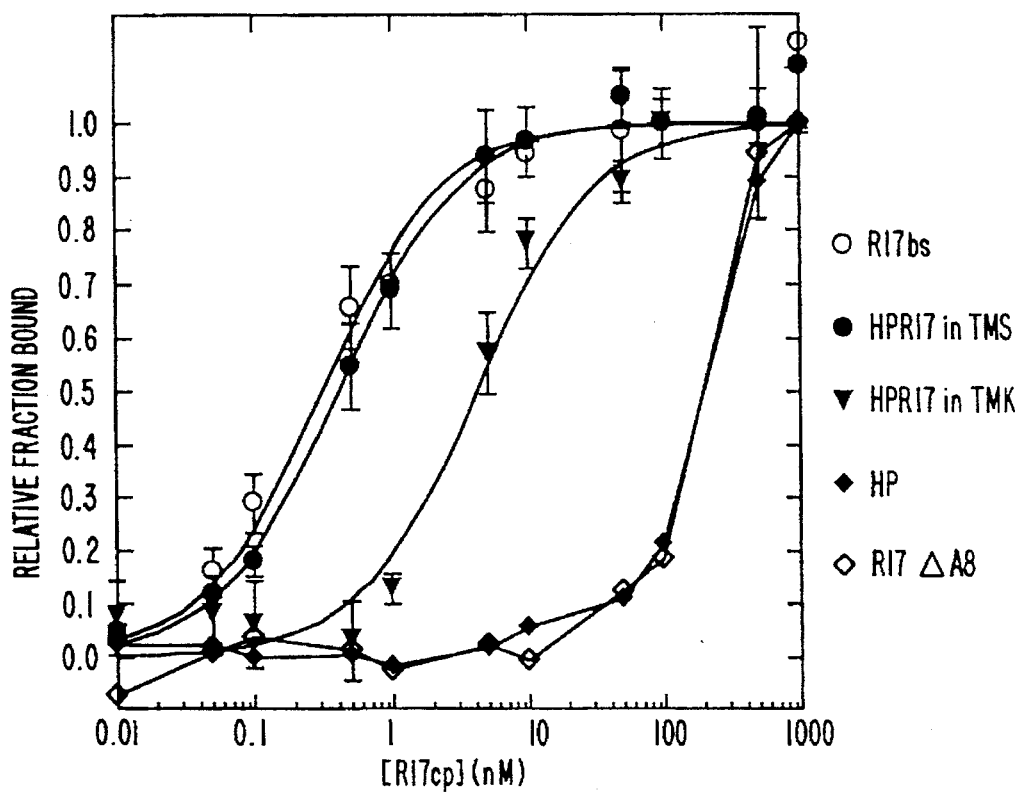

FIG. 9 shows binding of R17 coat protein to R17 binding site (R17bs), HpR17, Hp and R17bs containing a deletion of A8 (R17ΔA8).

Figure 10:
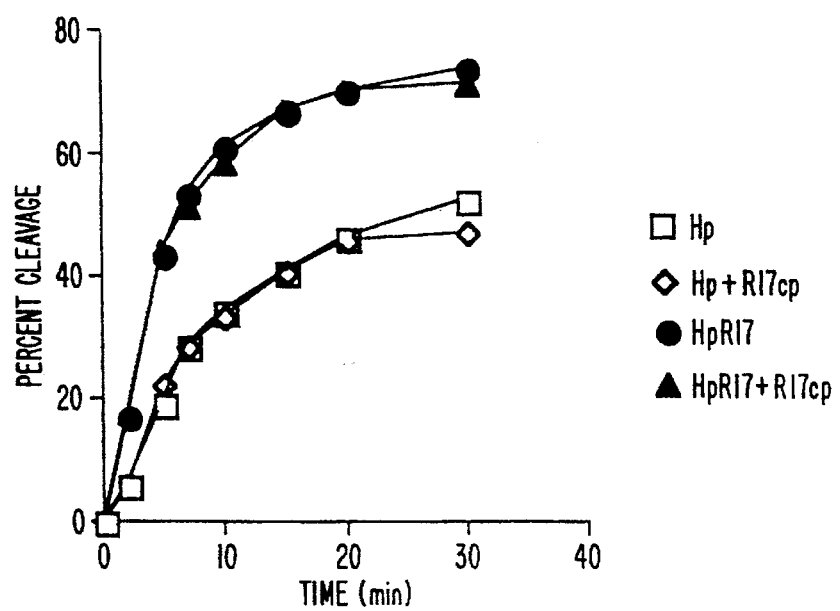

FIG. 10 shows the effect of R17 coat protein on RNA cleavage reactions catalyzed by Hp and R17Hp ribozymes.

Figure 11A:
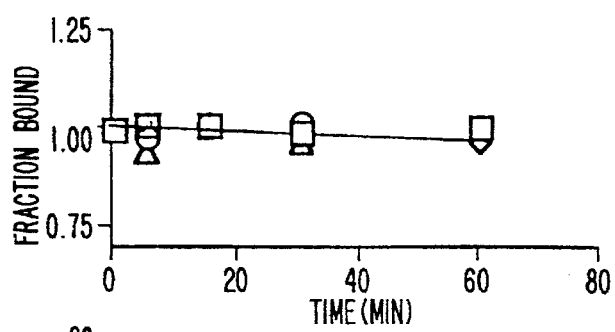
Figure 11B:
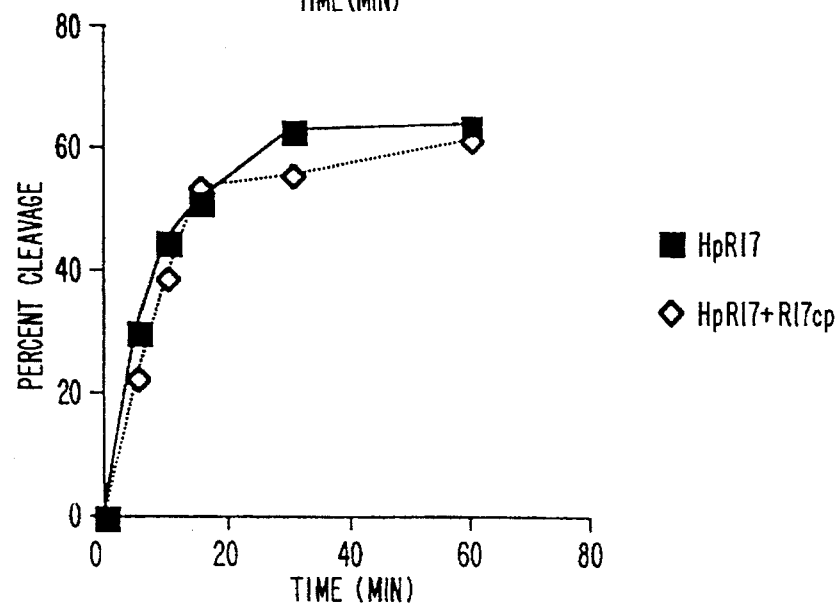
Figure 17A:
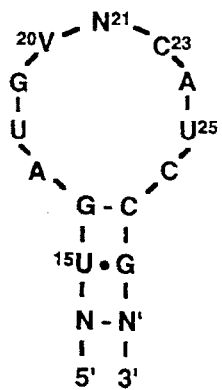
Figure 17B:
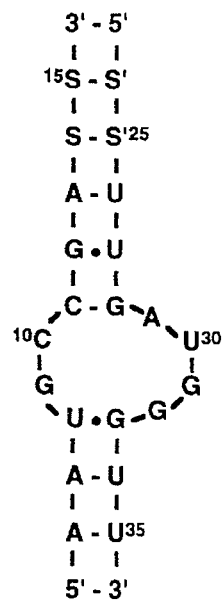
Figure 17C:
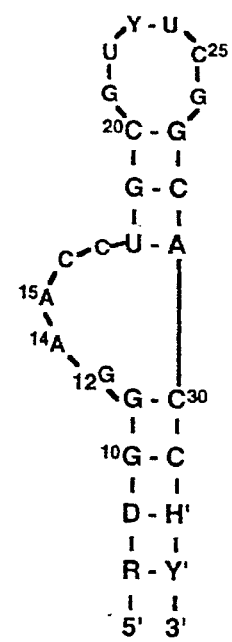
Figure 17D:
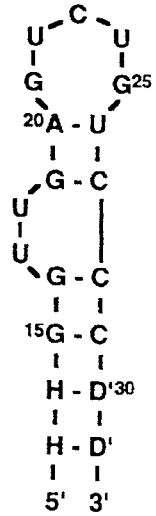
Figure 17E:
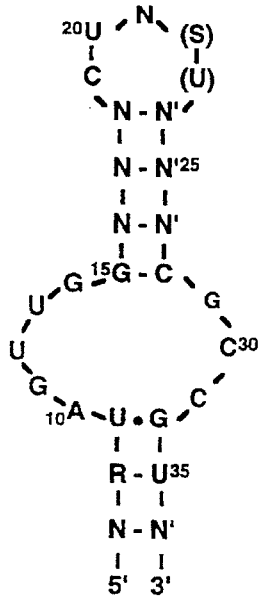
Figure 17F:
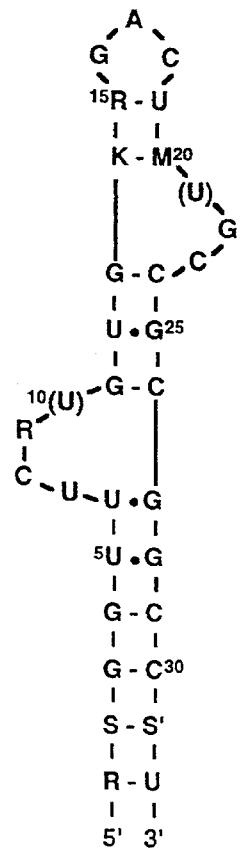

FIG. 11 shows that R17 coat protein is stably bound to the R17Hp ribozyme during RNA cleavage reaction.

Figure 12:
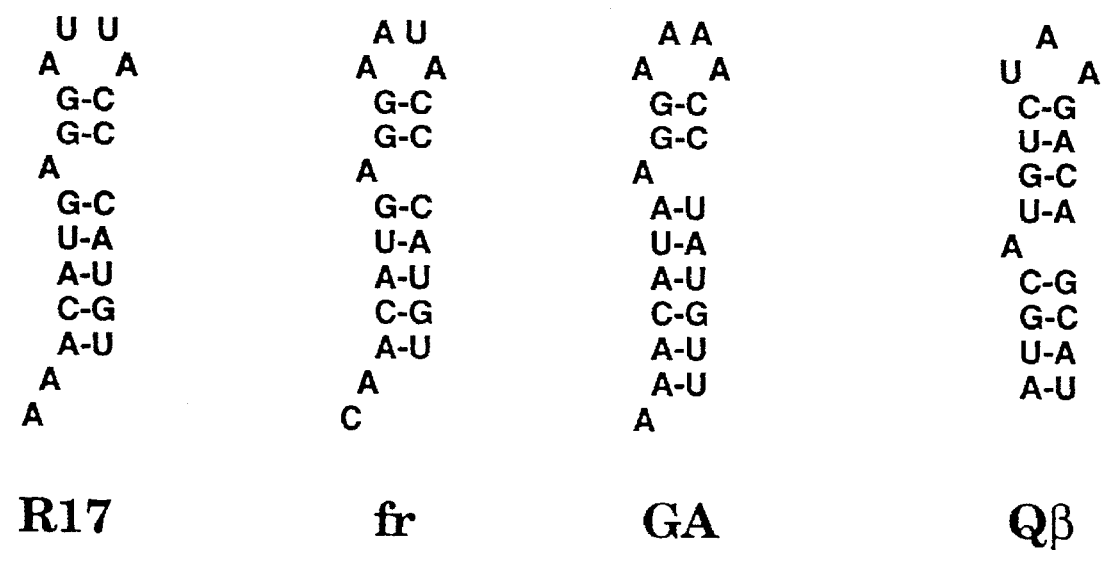

FIGS. 12 shows non-limiting examples of RNA structural motifs that bind to a bactriophage coat proteins. R17 (SEQ ID No. 10), fr (SEQ ID No. 11), GA (SEQ ID No. 12) and Qb (SEQ ID No. 13) are examples of RNA bactriophages (Witherell et al., supra).

FIG. 13 shows non-limiting examples of RNA structural motifs that bind cellular proteins (Witherell et al., supra). L1 (SEQ ID No. 14), L4 (SEQ ID No. 18) and L10 (SEQ ID No. 21) are ribosomal protein binding domains. The fat (SEQ ID No. 15) is the trans-activator protein encoded by HIV. 70K (SEQ ID No. 16) and p57 (SEQ ID No. 20) are mammalian RNA binding proteins. IREP (SEQ ID No. 19) is the iron responsive element binding protein. The motif of α-Sarcin (SEQ ID No. 17) is also shown.

FIG. 14 shows RNA binding elements (SEQ ID Nos. 22–25) that are recognized by HIV regulatory proteins (rev and tat). Minimal rev binding elements are as described by Bartel et al., 1991 (*Cell* 67, 1–20).

Figures 15, 16:
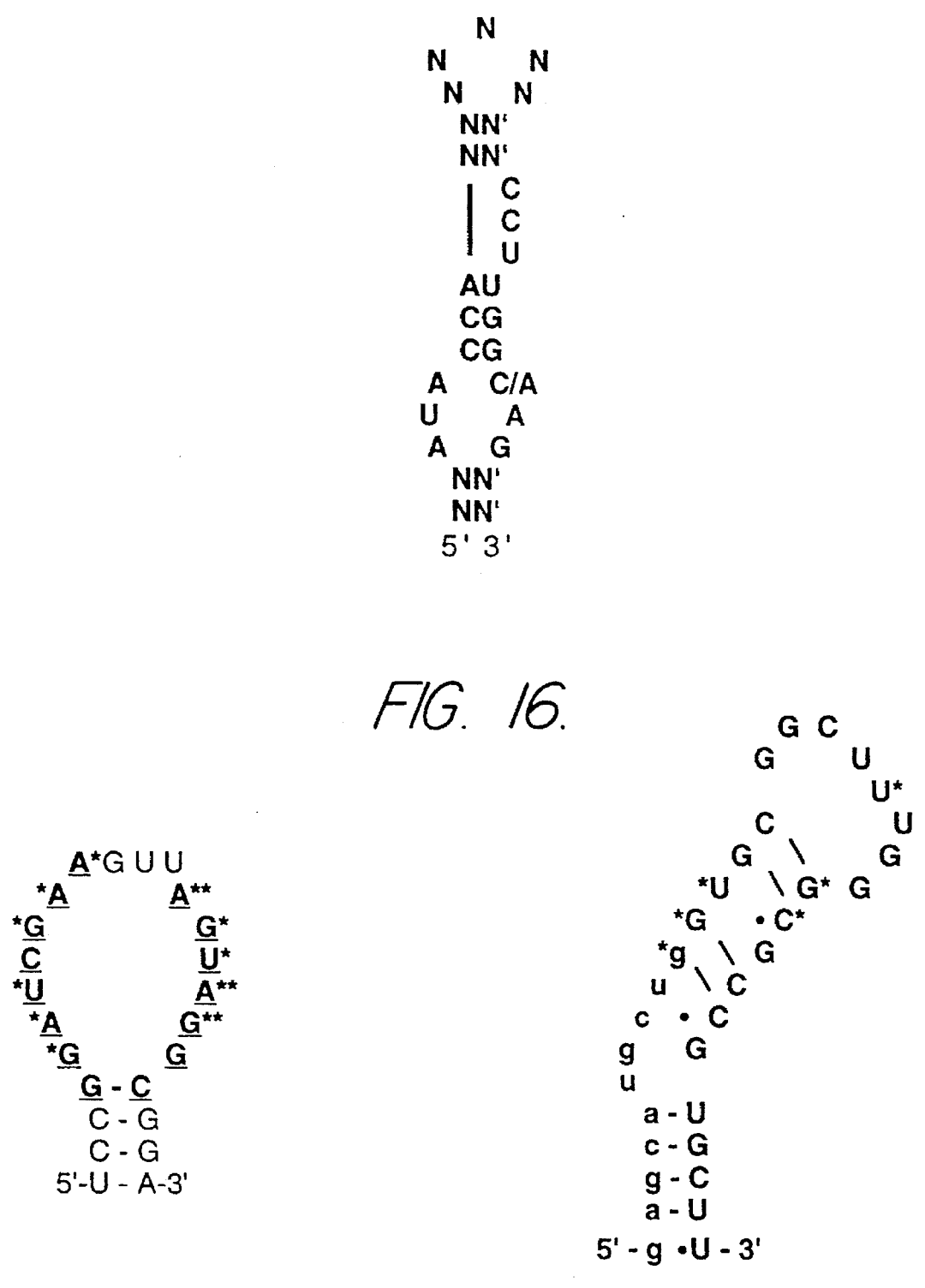

FIG. 15 shows the general structure of RNA motif (SEQ ID No. 26) that binds theophyline with high affinity (Jenison et al., 1994 *Science* 263, 1425). Theophylline is used to treat people suffering from asthma, bronchitis and emphysema.

FIG. 16 shows general structures of RNA motifs (SEQ ID Nos. 27 and 28) that binds thrombin with high affinity (Kubik et al., 1994 Nucleic Acids Res. 22, 2619).

FIG. 17 shows general structures of RNA motifs (SEQ ID Nos. 29–35) that binds vascular endothelial growth factor with high affinity (Jellinek et al., 1994 Biochemistry 33, 10450). R, purines; Y, pyrimidines; K, guanosine or uridine; M, adenosine or cytidine; S, guanosine or cytidine; D, adenosine, guanosine or uridine; H, adenosine, uridine or cytidine; V, guanosine, adenosine or cytidine; N, any base.

FIG. 18 shows various positions where ligand-binding motifs or domains can be inserted in a hairpin ribozyme (SEQ ID Nos. 6 and 7). Arrows indicate the sites of insertions. Similarly, ligand-binding domains can be readily inserted at various positions in other ribozymes, provided the catalytic activity of the ribozyme is not significantly effected.

Ribozymes

Synthesis of nucleic acids greater than 100 nucleotides in length is difficult using automated methods, and the therapeutic cost of such molecules is prohibitive. In this invention, small enzymatic nucleic acid motifs (e.g., of the hammerhead or the hairpin structure) are used for exogenous delivery. The simple structure of these molecules increases the ability of the enzymatic nucleic acid to invade targeted regions of the mRNA structure. However, these catalytic RNA molecules can also be expressed within cells from eukaryotic promoters (e.g., Scanlon et al., 1991, Proc. Natl. Acad. Sci. USA, 88, 10591-5; Kashani-Sabet et al., 1992 Antisense Res. Dev., 2, 3–15; Dropulic et al., 1992 J. Virol, 66, 1432-41; Weerasinghe et al., 1991 J. Virol, 65, 5531-4; Ojwang et al., 1992 Proc. Natl. Acad. Sci. USA 89, 10802-6; Chen et al., 1992 Nucleic Acids Res., 20, 4581-9; Sarver et al., 1990 Science 247, 1222–1225). Those skilled in the art realize that any ribozyme can be expressed in eucaryotic cells from the appropriate DNA vector. The activity of such ribozymes can be augmented by their release from the primary transcript by a second ribozyme (Draper et al., PCT WO 93/23569, and Sullivan et al., PCT WO 94/02595, both hereby incorporated in their totality by reference herein; Ohkawa et al., 1992 Nucleic Acids Symp. Ser., 27, 15-6; Taira et al., 1991, Nucleic Acids Res., 19, 5125-30; Ventura et al., 1993 Nucleic Acids Res., 21, 3249-55;Chowrira et al., 1994 J. Biol Chem. 269, 25856).

The following are examples of a hairpin ribozyme with a protein binding sequence provided in helix 4 and methods for its production and introduction into a cell. Those skilled in the art will recognize that this example is not limiting the invention and that other protein binding sequences can be readily provided in other locations (or in other ribozyme motifs) as noted above for single-stranded or double-stranded RNA binding proteins. If they are added at the 5' or 3' end of the ribozyme they can be provided as a hairpin loop to form the double-stranded RNA.

The following materials or methods were used in the following examples:

Material And Methods

Protein Purification

R17cp was purified from an E. coli overexpressing clone (pTCT5 in BL21 (IDE3)) kindly provided by Dr O. Uhlenbeck. Protein concentration was determined by optical density at 280 nM and by a Bradford assay (Bio-Rad protein assay) compared to known concentration of Bovine Serum Albumin. It was then stored in 1 mM acetic acid, 1 mM DTT at 4° C.

Construction of Plasmid pHpR17

All molecular manipulations were done according to Sambrook et al., 1989 (Mol. Cloning: A Lab. Manual, Cold Spring Harbor Laboratory Press). Briefly, two partially overlapping oligonucleotides encoding the self-cleaving HpR17 RNA (FIG. 2) and the bacteriophage T7 RNA polymerase promoter were annealed and converted into a double-stranded DNA. These sequences were cloned into pUC19 plasmid using Hind III and Sal I restriction sites. The identity of the positive clones were confirmed by sequencing the plasmid DNA using the Sequenase® II kit (U.S. Biochemicals).

RNA Preparation

RNAs were transcribed from a synthetic oligonucleotide template or from the Sal I linearized pHpR17 plasmid using bacteriophage T7 RNA polymerase as described (Milligan & Uhlenbeck, 1989 Methods Enzymol. 180, 51). RNAs were purified on 10 or 20% polyacrylamide gels containing 7M urea, visualized by UV shadowing, excised and eluted overnight at 4° C. in 500 mM ammonium acetate, 0.1% SDS and 1 mM EDTA. The RNA pellets were washed with 70% ethanol, dried, resuspended in water and quantified.

RNAs to be 5' end labeled were first dephosphorylated with calf intestinal phosphatase (1 unit/50 pmoles of RNA-Boheringer Mannheim) for 60 min at 50° C. and kinased using [$\lambda$-$^{32}$P] ATP and T4 polynucleotide kinase (U.S. Biochemicals). End-labeled RNAs were subsequently purified as described above.

Filter-Binding Assays

Association constants were determined by filter-binding assays (Carey et al., 1983 Biochemistry 22, 2601). Trace amount of labeled RNA (15–32 fmoles) was heat denatured and renatured in 500 μl of T.M.S buffer (40 mM Tris-HCl pH 8, 12 mM MgCl$_2$ and 2 mM spermidine) or TMK buffer (40 mM Tris-Acetate pH 8, 10 mM Mg.Acetate, 80 mM KCl). The reaction was initiated by adding R17 coat protein at various concentrations (0.01 nM to 1 μM). After at least 20 minutes of incubation at the desired temperature, 450 μl of the reaction mixture was filtered through pre-soaked nitrocellulose filter (Millipore-HAWP 024–0,45 μM). The amount of complex retained by the filter was determined by liquid scintillation counting. The amount of input RNA was determined by spotting a 20 μl aliquot of the reaction mixture on a filter. The fraction bound by the filter was plotted as a function of protein concentration. As previously described (Carey et al., supra; Schneider et al., 1992 J. Mol. Biol. 228, 862), the maximum amount of fraction complexed varied between 40 and 100% depending on the RNA preparation. Results were normalized to 100% of retention at saturation for purposes of calculations and to compare different experiments. Although a theoretical pseudo-first order binding curve does not always describe accurately the experimental data, data points were fitted to a curve describing theoretical bimolecular association (Pyle & Green, 1994 Biochemistry 33, 2716). Dissociation constant (Kd) values were then obtained from a non-linear least-square fit using sigmaplot software (Jandel Scientific). Standard error was calculated from the fit of the observed curve to the theoretical one (reported by the sigmaplot software).

Gel-Shift Assay for Protein-RNA Interactions

Visualization of RNA-protein complex on polyacrylamide gels was done essentially as described by Lowary and Uhlenbeck (15 Nucl. Acids Res. 10483, 1987). Trace amounts of 5' end-labeled RNA (10 pM) was denatured at 90° C. for 1 minute and then renatured for 20 minutes on ice in TMS buffer. The RNA was then incubated with increasing concentrations of coat protein (from 1 pM to 0.1 µM) for 2 hours on ice. Glycerol (5% final concentration) was added to the samples prior to loading on a 6% native polyacrylamide gel containing 12 mM magnesium acetate and 40 mM Tris-Acetate pH 7.5. Electrophoresis was carried out at 150 V for 10 hours at 4° C.

Gel-Shift Assay for RNA—RNA Interactions

Ribozyme-substrate interactions were studied by gel shift assay essentially as described by Fedor and Uhlenbeck (1990 Proc. Natl. Acad. Sci. USA 87, 1668). Trace amount of 5' end-labeled non-cleavable G+1A (Chowrira et al., 1991 Nature 354, 320) substrate analog (10 pM) was incubated with increasing amount of cold ribozyme (0, 0.1, 1, 10, 20, 50 100 nM). The mixture of G+1A and ribozyme was denatured for 1 minute at 90° C. followed by renaturation in TMS buffer for 2 hours on ice. Glycerol (5final concentration) was added to the samples prior to loading on a 6% native polyacrylamide gel containing 12 mM magnesium acetate and 40 mM Tris-Acetate pH 7.5. Electrophoresis was carried out at 11 W for 13 hours at 4° C.

Ribozyme Cleavage Assays

Single turnover cleavage rates were obtained from reactions carried out under "ribozyme excess" conditions. Ribozyme and substrate were denatured separately for 1 minute at 90° C., then renatured on ice for 20 minutes in the reaction buffer (TMS or TMK). The RNA samples were equilibrated at reaction temperature (25° or 37° C.) for 20 minutes. Reactions were initiated by mixing an equal volume of ribozyme and substrate mixtures and incubation at the reaction temperature. 10 µl aliquots were removed at regular time intervals and the reaction was quenched with an equal volume of urea loading buffer (10 M Urea, 20% sucrose, 0.5% SDS, 0.02% xylene cyanol, 0.02% bromophenol blue, 160 mM Tris-HCl pH7.5, 160 mM Boric acid, 4 mM EDTA) and freezing on dry ice. Reaction products were resolved on a 20% polyacrylamide/7M urea gel, and the bands were quantified using Phosphoranalyst scanner (Bio-Rad). Data were fitted by a linear regression to the equation $\ln(y)=-kt+b$ were y is the unreacted fraction of the product, t the time, and k the rate of reaction. Reactions were first order until 60% of the substrate was cleaved. Variation in the substrate concentration did not affect the reaction rate as long as it was kept below the ribozyme concentration. As the reaction rate was proportional to an increase in the ribozyme concentration, a value of $k_{cat}/K_M$ was obtained by dividing k by the ribozyme concentration (Chowrira et al., 1993 Biochemistry 32, 1088; Herschlag & Cech, 1990 Biochemistry 29, 10159).

Multiple-Turnover Kinetics

Reactions were carried out as described above under "substrate excess" conditions. Varying substrate concentrations (10–1000 nM) were used in the reaction keeping the ribozyme concentration (2 nM) and time (5 min) constant. Kinetic parameters were obtained using the "kcat" software (BioMetallics).

Ligation Assay

Self-cleaving hairpin ribozymes were transcribed from linear plasmid templates using T7 RNA polymerase (Milligan & Uhlenbeck, 1989 supra). The RNA undergoes self-cleavage during transcription giving rise to two cleavage products. The 5' cleavage product contains the ribozyme portion covalently linked to 5' fragment of the cleaved substrate (Rz-5'P). Since the transcription is carried out in the presence of [$\alpha$-$^{32}$P]CTP, the transcripts are internally labeled and can be visualized by gel electrophoresis and autoradiography. The Rz-5'P is gel-purified as described above and mixed with unlabeled 3' fragment of the substrate (3'P), containing 5' hydroxyl group. The Rz-5'P and 3'P mixture was denatured for 2 minutes at 90° C. and then incubated at 4° C. in TMS buffer. Reaction was stopped by the addition of an equal volume of loading buffer and the products were resolved on a 10% polyacrylamide/7M urea gel. Products were quantified using Phosphoranalyst scanner (Bio-Rad). The reaction rate ($k_{obs}$) was obtained as described above.

UV Cross-Linking

Cross-linking reactions were carried out as described (Butcher and Burke, 1994 Biochemistry 33, 992). Briefly, RNAs were denatured at 70° C. for 2 minutes and renatured for 20 minutes on ice in TMS buffer. 20 µl aliquots were irradiated at a distance of 1 cm with a 254 nm UV light. Reactions were directly loaded on to a 15% polyacrylamide/7M urea gel. Products were quantified using Phosphoranalyst scanner (Bio-Rad) as described above.

EXAMPLE 1

Figure 2A:
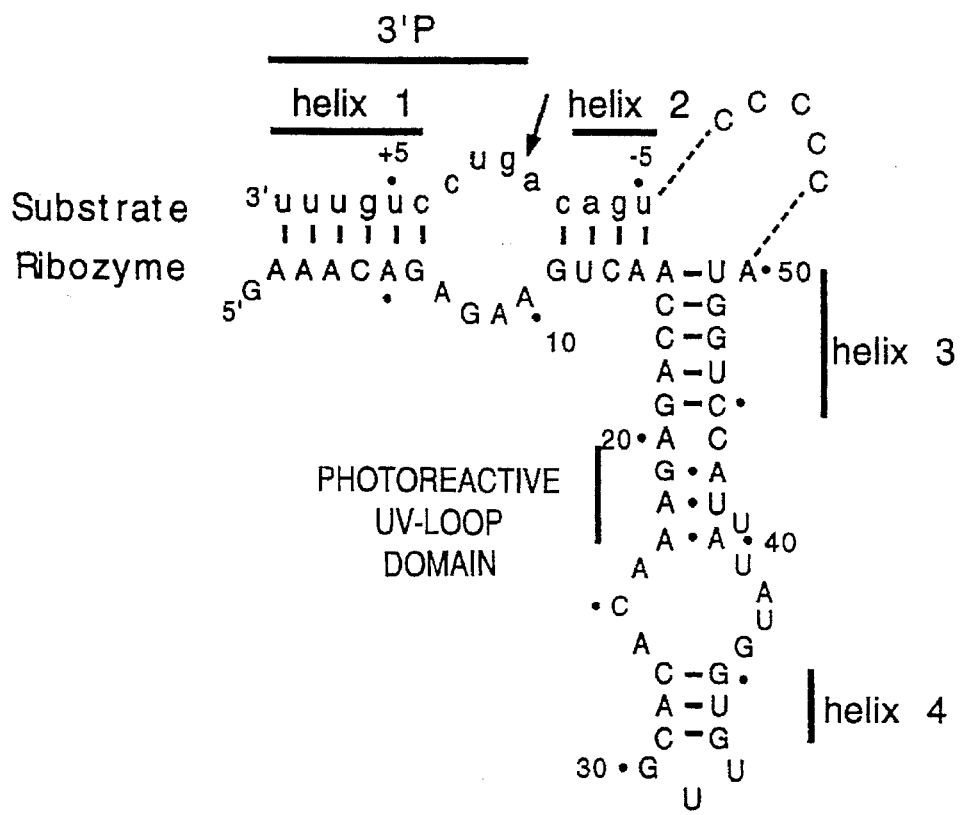
Figure 2B:
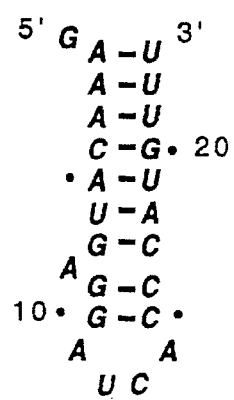
Figure 2C:
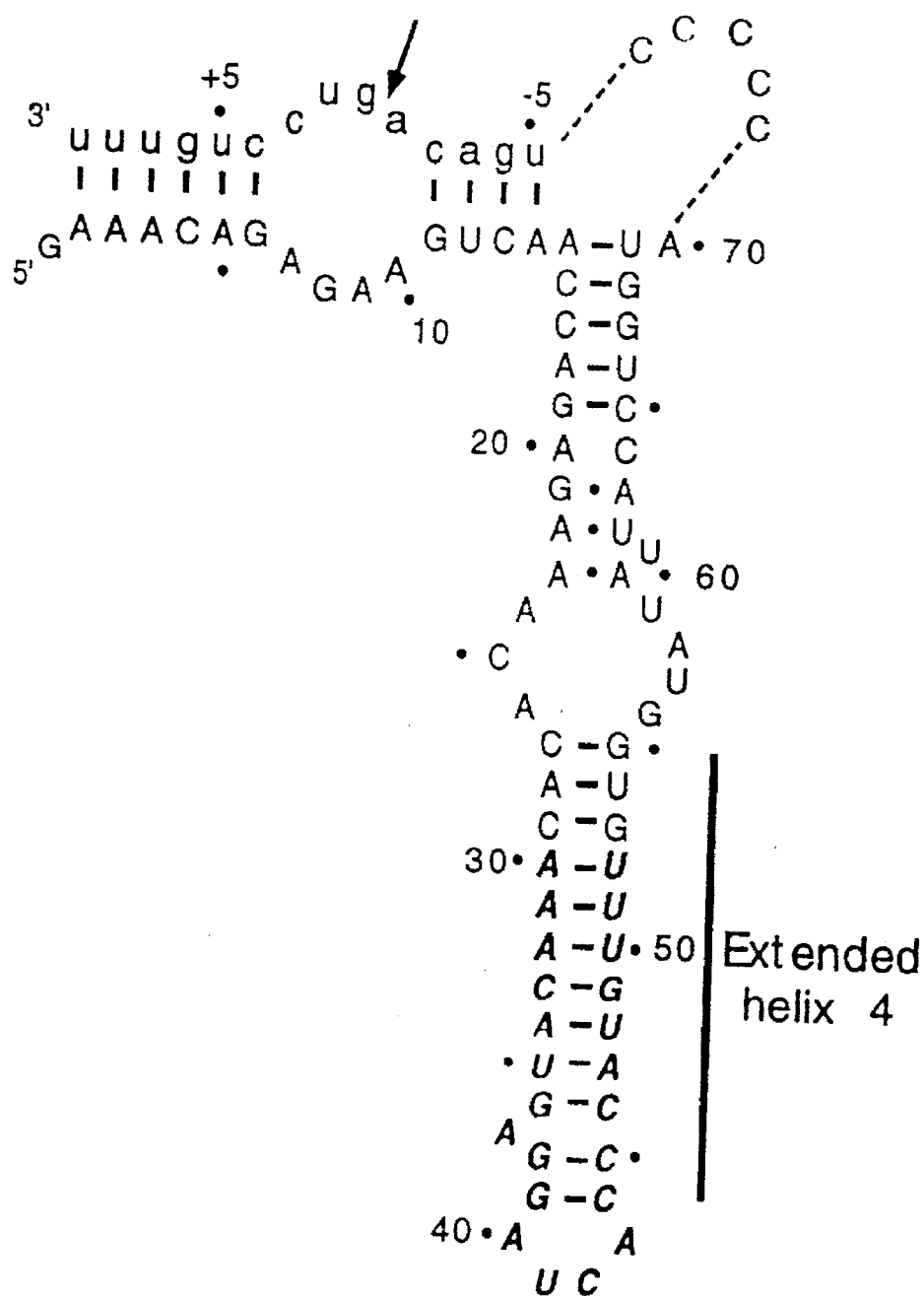

Insertion of a R17 Coat Protein Binding Site into the Hairpin Ribozyme Structure The R17 coat protein (R17cp) specifically binds a 23 nt RNA (R17bs) which forms a stable stem-loop structure (FIG. 2B; Witherell, et al., 1991 supra). Helix 4 of the hairpin ribozyme shows no sequence or length requirement (Berzal-Herranz et al., 1993 supra; Chowrira and Burke, 1992 supra; Anderson et al., 1994 supra) and the helix 4 loop can be deleted without effecting catalytic activity of the ribozyme (Chowrira & Burke, 1992 supra). Applicant has therefore introduced the R17bs in the helix 4 region of the hairpin ribozyme (FIG. 2C). The hairpin ribozyme containing the R17bs is designated HpR17.

Those skilled in the art will recognize that this example is non-limiting to the invention and that other protein binding sequences can be readily provided in other locations (or in other ribozyme motifs) as noted above for single-stranded or double-stranded RNA binding proteins. Those skilled in the art will recognize that the protein binding domain can be inserted at any position within a ribozyme (including the termini), as long as the catalytic activity of the ribozyme is not compromised.

EXAMPLE 2

Figure 6:
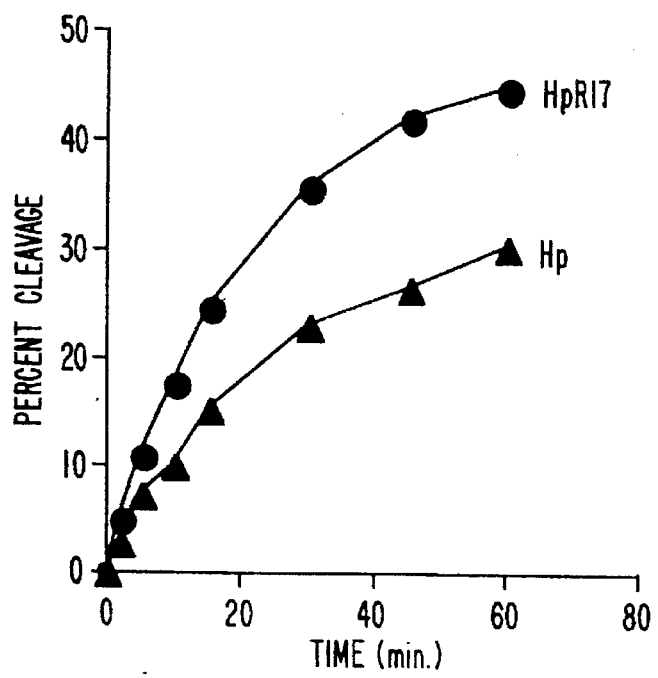
FIG. 6 shows a time course of RNA cleavage by Hp and HpR17 ribozymes.

The Protein Binding Domain increases the Rate of RNA Cleavage Reaction Catalyzed by the Ribozyme Referring to FIG. 6, RNA cleavage activity catalyzed by the Hp and the HpR17 ribozymes, in standard TMS buffer (TMS=40 mM Tris-HCl pH 7.5, 12 mM MgCl$_2$, 2 mM spermidine), were compared at 37° C. The elongated version of the hairpin ribozyme (HpR17) is 1.5 to 2 fold more active than the regular (Hp) ribozyme. Because buffers containing monovalent salts mimic more accurately the in vivo environment, we determined the effect of KCl on the catalytic rate. Increased catalytic efficiency of HpR17 ribozyme was consistently observed with different preparations of RNA, in presence or absence of monovalent salts, at 25° C. or 37° C. Determination of the Michaelis-Menten parameters of the reaction during multiple turn-over reactions showed that the improvement is mainly due to a slight increase in $k_{cat}$ (Table 2).

EXAMPLE 3

Figure 7:
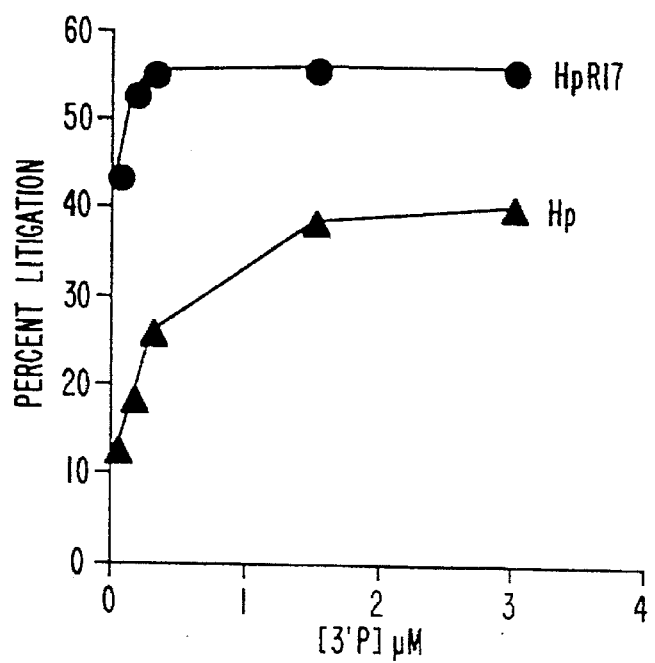
FIG. 7 shows RNA ligation reaction catalyzed by the Hp and HpR17 ribozymes.

The Protein Binding Domain Increases the Rate of RNA Ligation Reaction Catalyzed by the Ribozyme The self-cleavage reaction catalyzed by the hairpin ribozyme during transcription yields products wherein the 5' product contains the ribozyme linked to 5' cleaved fragment (Rz-5'P). The Rz-5'P fragment can catalyze a ligation reaction wherein a nucleic acid corresponding to 3' cleavage product (3'P) is ligated on to the 3' end Rz-5'P. Rates of ligation reaction catalyzed by Hp and HpR17 were compared (FIG. 7). The Hp ribozyme lacking the R17bs ligates only 30%–40% of the 3'P, while the HpR17 construct ligates ~60% of 3'P on to the 3' end of HpR17-5'P.

EXAMPLE 4

The Protein Binding Domain increases UV Cross-linking Efficiency

A high-efficiency UV-inducible cross-link within loop B of the hairpin was recently reported (Butcher & Burke, 1994, Biochemistry 33, 992; FIG. 2). Formation of this photo-reactive UV-loop domain is dependent on the integrity of a functional ribozyme structure. A UV cross-linking assay (Butcher & Burke, 1994, supra) was used to determine the structure of HpR17 ribozyme. Referring to FIG. 8, the HpR17 ribozyme UV cross-links approximately 2 fold faster than the Hp construct.

EXAMPLE 5

R17 Coat Protein Binds the HpR17 Ribozyme and the R17bs RNA with Similar Efficiencies A gel-shift assay is used to determine complex formation between RNA and R17cp. R17cp binds to R17bs and HpR17 RNA efficiently. No specific protein-RNA complexes were detected with Hp and R17ΔA8 (a null mutant binding site in which the bulged Adenine 8 is deleted and is used as a negative control; Carey et al., 1983 Biochemistry 22, 4723). Complex formation was observed at protein concentrations roughly equivalent to those previously reported (Lowary & Uhlenbeck, 1987 supra).

A filter binding assay (Carey, et al., 1983 Biochemistry 22, 2601) is used to confirm the results from gel-shift assay described above. Referring to FIG. 9, the R17cp binds to HpR17 as well as it binds to its genuine binding site (R17bs). In contrast, the binding curve for the Hp ribozyme is similar to the one observed with the null-mutant R17ΔA8 (Carey, et al., 1983 supra). Therefore the protein does not bind specifically to the hairpin ribozyme but introduction of the binding site sequences are sufficient to enable R17cp to bind efficiently to HpR17 ribozyme. The protein was also unable to recognize and bind to the substrate RNA alone.

The of R17cp binding was assayed in the presence of standard ribozyme reaction buffer (TMS) and in a more physiological buffer (TMK=Tris-Ac pH 7 40 mM, Mg(OAc)$_2$ 12 mM, KCl 80 mM) at 37° C. or 25° C. The Kd values are in good agreement with previous studies (Carey, et al., 1983 supra; Lowary & Uhlenbeck, 1987 supra; Schneider, et al., 1992 supra). As previously described, the efficiency of R17cp binding decreases with variations in temperature and ionic strength (Carey et al., 1983 supra). To prevent degradation by cellular ribonucleases that may have copurified with R17cp, applicant added ATA (aurintricarboxylic acid) in the reaction buffer. The binding properties were not affected by the presence of 0.1 mM ATA.

EXAMPLE 6

Binding of R17cp to HpR17 does not effect RNA Cleavage/Ligation Reactions Catalyzed by the Ribozyme Referring to FIG. 10, no significant differences were observed in the efficiency of RNA cleavage reactions catalyzed by the HpR17 ribozyme in the presence of increasing concentrations of R17 coat protein (from $10^{-10}$M to $10^{-6}$M). Detailed analysis of the ribozyme activity in the presence of the R17cp (0.5 μM) was carried such that all RNA molecules are complexed by the R17cp.

Additionally, the ligation reaction catalyzed by the HpR17 ribozyme, at 0° C., is insensitive to the presence of saturating concentrations of the R17cp. These results have been consistently obtained with different preparations of protein and RNA.

EXAMPLE 7

R17 Coat Protein is Bound to the HpR17 Ribozyme throughout the RNA Cleavage Reaction Applicant has shown that the R17cp binds to the HpR17 ribozyme and that the ribozyme functions efficiently in the presence of saturating concentration of the protein (see above). However, these results do not show that the ribonucleoprotein is actually responsible for the observed catalytic activity. To address this issue applicant first determined the protein affinity for HpR17 in the presence of a large excess of ribozyme over the substrate (under "ribozyme excess" RNA cleavage conditions). Applicant did not detect any differences in R17cp binding to the HpR17 ribozyme in the presence or absence of the substrate. Although the protein binds to the HpR17 under cleavage conditions, the possibility remains that the protein may quickly dissociate and re-associate while the reaction is taking place. To rule out this possibility, applicant monitored the protein-ribozyme complex stability during catalysis. In these experiments, the protein-ribozyme complex was pre-formed, and the cleavage reaction was initiated by adding the substrate in presence of a large excess of R17 binding site (R17bs) RNA. Excess R17bs is added to trap R17cp that may dissociate from the complex during catalysis. Under these conditions, the HpR17-R17cp complex is stable for over an hour, during which most of the target RNA has been cleaved. The extreme stability of the complex is not surprising, as Lowary and Uhlenbeck showed that this RNA-protein complex has a half life of about 7 hours in TMK and over 24 h in low salt buffer at 0° C. (Lowary & Uhlenbeck, 1987 supra).

As the ligation was carried at 0° C., we assume that this reaction is also catalyzed by the ribonucleoprotein.

Elongating helix 4 with other sequences enhances the ribozyme activity (Anderson, et al., 1994). This shows that the increase in catalytic efficiency may simply be due to helix 4 stabilization, and that the helix 4 terminus is likely to be oriented away from essential structural elements.

Interestingly, stabilization of helix 4 also results in stabilization of a catalytically essential tertiary structure within loop B of the ribozyme, as monitored by UV cross-linking (FIG. 8).

Ribozymes engineered to cleave foreign target RNA sequences are sometimes accompanied by a loss in the catalytic efficiency of that ribozyme. The 2-fold increase in cleavage associated with the HpR17 ribozyme may significantly improve the efficiency of ribozymes engineered to cleave a foreign target, especially, if introduced in combination with base substitutions that have been previously shown to act as general catalysis enhancing mutations of the ribozyme (Berzal-Herranz, et al., 1993 supra).

The present invention shows that a ribozyme can function as a ribonucleoprotein. The R17 coat-protein is part of a class of stem-loop RNA binding proteins that are common in prokaryotes and eukaryotes, and the results obtained here can be extended to other proteins (see FIGS. 12–17). It has recently been shown that a ribozyme can recruit non-specific RNA binding proteins to improve its activity (Bertrand & Rossi, 1994 *EMBO. J* 13, 2904; Coetze, et al., 1994 supra; Herschlag et al., 1994 *EMBO. J.* 13, 2913; Tsuchihaschi et al., 1993, *Science* 262, 99–102).

The present invention features a ribozyme able to tightly bind to a specific RNA binding protein, which may have significant therapeutic applications; for example, it could be used to co-localize the ribozyme to its target within a cell, where RNAs are not homogeneously dispatched. It has been shown on several instances that RNAs are directed towards specific locations in the nucleus or the cytoplasm (Wilhelm & Vale, 1993 *J. Cell Biol* 123, 269). Sullenger and Cech (1993 *Science* 262, 1566) have introduced a ribozyme into a defective virus DNA sequence. The resulting chimeric transcript follows the same pathways as the viral RNA lacking the ribozyme and is therefore co-localized with target RNAs in the viral nucleocapsid. This strategy was shown to be effective in improving the ribozyme activity in vivo. An alternative way of directing the ribozyme to a desired location is to attach, to a ribozyme, a binding site for a protein known to be localized close to the targeted RNA (e.g., ribosomal proteins), or known to be involved in RNA transport (e.g., certain small nuclear ribonucleoproteins).

Applicant has shown in the present invention that a model HpR17 ribozyme can actually function as a ribonucleoprotein. Other engineered hairpin ribonucleoproteins also be readily generated. For example, the introduction of a portion of the Rev binding element (FIG. 14A) in the hairpin ribozyme could be used to co-localize the ribozyme with HIV mRNA (Cohli et al., 1994 *Antisense Res. Develop.* 4, 19).

Specific interactions between RNA and proteins are known to be involved in RNA stability and viral packaging. Depending on the protein used, a ribozyme (ribonucleoprotein) can be used to stabilize the RNA in the cell, and enable efficient transport of the ribozyme in an organism along with the targeted virus. The presence of the R17 binding site in a RNA sequence is sufficient to promote its encapsidation by the virus (Pickett & Peabody, 1993 *Nucleic Acids Res.* 21, 4621). Such a system could be used to transport copies of a ribozyme among a population of cells, like procaryotic cell population or inside a plant or an animal.

The presence of the protein can enhance in vivo stability by protecting the ribozyme from cellular nucleases and may also prevent non-specific proteins from interfering with the ribozyme activity.

In vitro Evolution

Protein binding domains described in the present invention can also be used to regulate ribozyme activity. In vitro evolution strategies (see Joyce, 1992 *Scientific American* 267, 90) are used to evolve for a protein binding-dependent ribozyme. A protein-dependent ribozyme is a useful tool for in vivo applications: e.g., it would allow the engineering of ribozymes specific for a cell type or a cell infected by a virus.

In vitro evolution strategies can also be used to evolve ribozymes that would be inhibited by binding of a specific protein to the designated binding site. Such protein-dependent catalytic RNA could also be studied as a model system for the demonstrated or supposed cellular protein dependent ribozymes: group I and II introns, RNase P, ribosome spliceosome (see for example Mohr et al., 1994 *Nature* 370, 147).

The in vitro selection (evolution) strategy is similar to approaches developed by Joyce (Beaudry and Joyce, 1992 *Science* 257, 635; Joyce, 1992 Supra), Szostak (Bartel and Szostak, 1993 *Science* 261,1411; Szostak, 1993 *TIBS* 17, 89) and Burke (Berzal-Herranz et al., 1992 *Genes & Develop.* 6, 129). Briefly, a random pool of nucleic acids is synthesized wherein, each member contains two domains: a) one domain consists of a region with defined (known) nucleotide sequence; b) the second domain consists of a region with degenerate (random) sequence. The known nucleotide sequence domain enables: 1) the nucleic acid to bind to its target (the region flanking the mutant nucleotide), 2) complementary DNA (cDNA) synthesis and PCR amplification of molecules selected for their desired activity (e.g., protein binding) 3) introduction of restriction endonuclease site for the purpose of cloning. The degenerate domain can be created to be completely random (each of the four nucleotides represented at every position within the random region) or the degeneracy can be partial (Beaudry and Joyce, 1992 supra). This random library of nucleic acids is incubated under conditions that ensure folding of the nucleic acids into conformations that facilitate the desired activity (e.g., protein binding). Following incubation, nucleic acids are converted into complementary DNA (if the starting pool of nucleic acids is RNA). Nucleic acids with desired trait (e.g., protein binding) can be separated from rest of the population of nucleic acids by using a variety of methods. For example, a filter-binding assay can be used to separate the fraction that binds the desired protein from those that do not. The fraction of the population that is bound by the protein (for example) is the population that is desired (active pool). A new piece of DNA (containing new oligonucleotide primer binding sites for PCR and RE sites for cloning) is introduced to the termini of the active pool (to reduce the chances of contamination from previous cycles of selection) to facilitate PCR amplification and subsequent cycles (if necessary) of selection. The final pool of nucleic acids with the desired trait is cloned in to a plasmid vector and transformed into bacterial hosts. Recombinant plasmids can then be isolated from transformed bacteria and the identity of clones can be determined using DNA sequencing techniques.

Target Sites

Targets for useful ribozymes can be determined as disclosed in Draper et al. WO 93/23569 Sullivan et al., WO 94/02595 as well as by Draper et al., "Method and reagent for treatment of arthritic conditions" U.S. Ser. No. 08/152, 487, filed Nov. 12, 1993, and hereby incorporated by reference herein in totality. Rather than repeat the guidance provided in those documents here, below are provided specific examples, not limiting to those in the art. Ribozymes to such targets are designed as described in those applications and synthesized to be tested in vitro and in vivo, as also described. Such ribozymes can also be optimized and delivered as described therein.

Ribozymes are designed to anneal to various sites in the target RNA. The binding arms are complementary to the target site sequences described above. The ribozymes are chemically synthesized. The method of synthesis used follows the procedure for normal RNA synthesis as described in Usman et al., 1987 *J. Am. Chem. Soc.* 109, 7845, and in Scaringe et al., 1990 *Nucleic Acids Res.* 18, 5433, and makes use of common nucleic acid protecting and coupling groups, such as dimethoxytrityl at the 5'-end, and phosphoramidites at the 3'-end. The average stepwise coupling yields were >98%. Hairpin ribozymes are synthesized in two parts and annealed to reconstruct the active ribozyme (Chowrira and Burke, 1992 *Nucleic Acids Res.*, 20, 2835). Alternately, ribozymes can also be transcriptionally synthesized using bacteriophage RNA polymerase, foe example, T7 RNA polymerase. Ribozymes are modified extensively to enhance stability by modification with nuclease resistant groups, for example, 2'-amino, 2'-C-allyl, 2'-flouro, 2'-o-methyl, 2'-H (for a review see Usman and Cedergren, 1992 *TIBS* 17, 34). Ribozymes are purified by gel electrophoresis using general methods or are purified by high pressure liquid chromatography (HPLC; See Usman et al., Synthesis, deprotection, analysis and purification of RNA and ribozymes, filed May, 18, 1994, U.S. Ser. No. 08/245,736 the totality of which is hereby incorporated herein by reference) and are resuspended in water.

Ribozyme activity can be optimized by chemically synthesizing ribozymes with modifications that prevent their degradation by serum ribonucleases (see e.g., Eckstein et al., International Publication No. WO 92/07065; Perrault et al., 1990 *Nature* 344:565; Pieken et al., 1991 Science 253:314; Usman and Cedergren, 1992 supra; Usman et al., International Publication No. WO 93/15187; and Rossi et al., International Publication No. WO 91/03162, as well as Usman, N. et al. U.S. patent application Ser. No. 07/829,729, and Sproat, B. European Patent Application 92110298.4; Ortigao et al., 2 *Antisense Research and Development;* Krist et al., Abstracts International conference on antisense nucleic acids, Garmisch-Partenkirchen, 1993; Chowrira and Burke, 1992 supra; Chowrira et al., 1993 *J. Biol. Chem.* 268, 19458, which describe various chemical modifications that can be made to the sugar moieties of enzymatic RNA molecules. All these publications are hereby incorporated by reference herein.), modifications which enhance their efficacy in cells, and removal of helix-containing bases to shorten RNA synthesis times and reduce chemical requirements.

Ribozymes are added directly, or can be complexed with cationic lipids, packaged within liposomes, or otherwise delivered to target cells. The RNA or RNA complexes can be locally administered to relevant tissues ex vivo, or in vivo through injection, aerosol inhalation, infusion pump or stent, with or without their incorporation in biopolymers.

Sullivan, et al., supra, describes the general methods for delivery of enzymatic RNA molecules. Ribozymes may be administered to cells by a variety of methods known to those familiar to the art, including, but not restricted to, encapsulation in liposomes, by iontophoresis, or by incorporation into other vehicles, such as hydrogels, cyclodextrins, biodegradable nanocapsules, and bioadhesive microspheres.

For some indications, ribozymes may be directly delivered ex vivo to cells or tissues with or without the aforementioned vehicles. Alternatively, the RNA/vehicle combination is locally delivered by direct injection or by use of a catheter, infusion pump or stent. Other routes of delivery include, but are not limited to, intravascular, intramuscular, subcutaneous or joint injection, aerosol inhalation, oral (tablet or pill form), topical, systemic, ocular, intraperitoneal and/or intrathecal delivery. More detailed descriptions of ribozyme delivery and administration are provided in Sullivan, et al., supra and Draper, et al., supra which have been incorporated by reference herein.

Another means of accumulating high concentrations of a ribozyme(s) within cells is to incorporate the ribozyme-encoding sequences into a DNA expression vector. Transcription of the ribozyme sequences are driven from a promoter for eukaryotic RNA polymerase I (pol I), RNA polymerase II (pol II), or RNA polymerase III (pol III). Transcripts from pol II or pol III promoters will be expressed at high levels in all cells; the levels of a given pol II promoter in a given cell type will depend on the nature of the gene regulatory sequences (enhancers, silencers, etc.) present nearby. Prokaryotic RNA polymerase promoters are also used, providing that the prokaryotic RNA polymerase enzyme is expressed in the appropriate cells (Elroy-Stein, O. and Moss, B., 1990, *Proc. Natl. Acad. Sci. USA,* 87, 6743–7; Gao, X. and Huang, L., 1993, *Nucleic Acids Res.,* 21, 2867–72; Lieber, A., et al., 1993, *Methods Enzymol.,* 217, 47–66; Zhou, Y., et al., 1990, *Mol. Cell. Biol.,* 10, 4529–37). Several investigators have demonstrated that ribozymes expressed from such promoters can function in mammalian cells (e.g. Kashani-Sabet, M., et al., 1992, *Antisense Res. Dev.,* 2, 3–15; Ojwang, J. O., et al., 1992, *Proc. Natl. Acad. Sci. USA,* 89, 10802–6; Chen, C. J., et al., 1992, *Nucleic Acids Res.,* 20, 4581–9; Yu, M., et al., 1993, *Proc. Natl. Acad. Sci. USA,* 90, 6340–4; L'Huillier, P. J., et al., 1992, *EMBO J.,* 11, 4411–8; Lisziewicz, J., et al., 1993, *Proc. Natl. Acad. Sci. U.S.A.,* 90, 8000–4)). The activity of such ribozymes can be augmented by their release from the primary transcript by a second ribozyme (Draper et al., PCT WO93/23569, and Sullivan et al., PCT WO94/02595, both hereby incorporated in their totality by reference herein; Ohkawa et al., 1992 *Nucleic Acids Symp. Ser,* 27, 15–6; Taira et al., 1991, *Nucleic Acids Res.,* 19, 5125–30; Ventura et al., 1993 *Nucleic Acids Res.,* 21, 3249–55; Chowrira et al., 1994 *J. Biol. Chem.* 269, 25856). The above ribozyme transcription units can be incorporated into a variety of vectors for introduction into mammalian cells, including but not restricted to, plasmid DNA vectors, viral DNA vectors (such as adenovirus or adeno-associated vectors), or viral RNA vectors (such as retroviral, Semliki forest virus, sindbis virus vectors).

In a preferred embodiment of the invention, a transcription unit expressing a hairpin ribozyme that cleaves target RNA is inserted into a plasmid DNA vector or an adenovirus or adeno-associated DNA viral vector. Both viral vectors have been used to transfer genes to the lung and both vectors lead to transient gene expression (Zabner et al., 1993 *Cell* 75, 207; Carter, 1992 *Curr. Opi. Biotech.* 3, 533) and both vectors lead to transient gene expression. The adenovirus vector is delivered as recombinant adenoviral particles. DNA may be delivered alone or complexed with vehicles (as described for RNA above). The DNA, DNA/vehicle complexes, or the recombinant adenovirus particles are locally administered to the site of treatment, e.g., through the use of an injection catheter, stent or infusion pump or are directly added to cells or tissues ex vivo.

In another aspect of the invention, ribozymes that cleave target molecules are expressed from transcription units inserted into DNA, RNA, or viral vectors. Preferably, the recombinant vectors capable of expressing the ribozymes are locally delivered as described above, and transiently persist in target cells. Once expressed, the ribozymes cleave the target mRNA. The recombinant vectors are preferably DNA plasmids, adenovirus, retroviral or adeno-associated virus vectors. However, other mammalian cell vectors that direct the expression of RNA may be used for this purpose.

Thus, ribozymes of the present invention that cleave target mRNA and thereby inhibit and/or reduce target activity have many potential therapeutic uses, and there are reasonable modes of delivering the ribozymes in a number of the possible indications. Development of an effective ribozyme that inhibits specific function are described in the art.

By "inhibit" is meant that the activity or level of target RNA is reduced below that observed in the absence of the ribozyme, and preferably is below that level observed in the presence of an inactive RNA molecule able to bind to the same site on the RNA, but unable to cleave that RNA.

By "vectors" is meant any nucleic acid- and/or viral-based technique used to deliver a desired nucleic acid.

Diagnostic Uses

Ribozymes of this invention may be used as diagnostic tools to examine genetic drift and mutations within diseased cells, or to detect specific RNA molecules, such as virus RNA. The close relationship between ribozyme activity and the structure of the target RNA allows the detection of mutations in any region of the molecule which alters the base-pairing and three-dimensional structure of the target RNA. By using multiple ribozymes described in this invention, one may map nucleotide changes which are important to RNA structure and function in vitro, as well as in cells and tissues. Cleavage of target RNAs with ribozymes may be used to inhibit gene expression and define the role (essentially) of specified gene products in the progression of disease. In this manner, other genetic targets may be defined as important mediators of the disease. These experiments will lead to better treatment of the disease progression by affording the possibility of combinational therapies (e.g., multiple ribozymes targeted to different genes, ribozymes coupled with known small molecule inhibitors, or intermittent treatment with combinations of ribozymes and/or other chemical or biological molecules). Other in vitro uses of ribozymes of this invention are well known in the art, and include detection of the presence of mRNA associated with a related condition. Such RNA is detected by determining the presence of a cleavage product after treatment with a ribozyme using standard methodology.

In a specific example, ribozymes which can cleave only wild-type or mutant forms of the target RNA are used for the assay. The first ribozyme is used to identify wild-type RNA present in the sample and the second ribozyme will be used to identify mutant RNA in the sample. As reaction controls, synthetic substrates of both wild-type and mutant RNA will be cleaved by both ribozymes to demonstrate the relative ribozyme efficiencies in the reactions and the absence of cleavage of the "non-targeted" RNA species. The cleavage products from the synthetic substrates will also serve to generate size markers for the analysis of wild-type and mutant RNAs in the sample population. Thus each analysis will require two ribozymes, two substrates and one unknown sample which will be combined into six reactions. The presence of cleavage products will be determined using an RNAse protection assay so that full-length and cleavage fragments of each RNA can be analyzed in one lane of a polyacrylamide gel. It is not absolutely required to quantify the results to gain insight into the expression of mutant RNAs and putative risk of the desired phenotypic changes in target cells. The expression of mRNA whose protein product is implicated in the development of the phenotype is adequate to establish risk. If probes of comparable specific activity are used for both transcripts, then a qualitative comparison of RNA levels will be adequate and will decrease the cost of the initial diagnosis. Higher mutant form to wild-type ratios will be correlated with higher risk whether RNA levels are compared qualitatively or quantitatively.

Other embodiments are within the following claims.

---

SEQUENCE LISTING ( 1 ) GENERAL INFORMATION:

( i i i ) NUMBER OF SEQUENCES: 35

( 2 ) INFORMATION FOR SEQ ID NO: 1:

( i ) SEQUENCE CHARACTERISTICS:
        ( A ) LENGTH: 11 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for any base.
        The letter "H"stands for C, A or U.

( x i ) SEQUENCE DESCRIPTION: SEQ ID NO: 1:

NNNNUHNNNN N        11

( 2 ) INFORMATION FOR SEQ ID NO: 2:

( i ) SEQUENCE CHARACTERISTICS:
    ( A ) LENGTH: 28 base pairs
    ( B ) TYPE: nucleic acid
    ( C ) STRANDEDNESS: single
    ( D ) TOPOLOGY: linear ( i x ) FEATURE:
    ( D ) OTHER INFORMATION: The letter "N" stands for any base.

( x i ) SEQUENCE DESCRIPTION: SEQ ID NO: 2:

NNNNNCUGAN GAGNNNNNNC GAAANNNN    28

( 2 ) INFORMATION FOR SEQ ID NO: 3:

( i ) SEQUENCE CHARACTERISTICS:
    ( A ) LENGTH: 70 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 3:

GAAACAGAGA AGUCAACCAG AGAAACACAC GUUGUGGUAU AUUACCUGGU ACCCCUGAC    60

AGUCCUGUUU    70

( 2 ) INFORMATION FOR SEQ ID NO: 4:

( i ) SEQUENCE CHARACTERISTICS:
    ( A ) LENGTH: 24 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 4:

GAAACAUGAG GAUCACCCAU GUUU    24

( 2 ) INFORMATION FOR SEQ ID NO: 5:

( i ) SEQUENCE CHARACTERISTICS:
    ( A ) LENGTH: 90 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 5:

GAAACAGAGA AGUCAACCAG AGAAACACAC AAACAUGAGG AUCACCCAUG UUUGUGGUAU    60

AUUACCUGGU ACCCCUGAC AGUCCUGUUU    90

( 2 ) INFORMATION FOR SEQ ID NO: 6:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( i x ) FEATURE:
    ( D ) OTHER INFORMATION: The letter "N" stands for any base.
    The letter "Y" stands for U or C.
    The letter "H" stands for A, U or C.

( x i ) SEQUENCE DESCRIPTION: SEQ ID NO: 6:

NNNNNNNYNG HYNNN    15

( 2 ) INFORMATION FOR SEQ ID NO: 7:

( i ) SEQUENCE CHARACTERISTICS:
    ( A ) LENGTH: 47 base pairs (B) TYPE: nucleic acid
(C) STRANDEDNESS: single
(D) TOPOLOGY: linear (ix) FEATURE:
(D) OTHER INFORMATION: The letter "N" stands for any base.
The letter "H" stands for A, U or C.

(xi) SEQUENCE DESCRIPTION: SEQ ID NO: 7:

NNNNGAAGNN NNNNNNNNNA AAHANNNNNN NACAUUACNN NNNNNNN 47

(2) INFORMATION FOR SEQ ID NO: 8:

(i) SEQUENCE CHARACTERISTICS:
(A) LENGTH: 85 base pairs
(B) TYPE: nucleic acid
(C) STRANDEDNESS: single
(D) TOPOLOGY: linear (xi) SEQUENCE DESCRIPTION: SEQ ID NO: 8:

UGGCCGGCAU GGUCCCAGCC UCCUCGCUGG CGCCGGCUGG GCAACAUUCC GAGGGGACCG 60

UCCCCUCGGU AAUGGCGAAU GGGAC 85

(2) INFORMATION FOR SEQ ID NO: 9:

(i) SEQUENCE CHARACTERISTICS:
(A) LENGTH: 176 base pairs
(B) TYPE: nucleic acid
(C) STRANDEDNESS: single
(D) TOPOLOGY: linear (xi) SEQUENCE DESCRIPTION: SEQ ID NO: 9:

GGGAAAGCUU GCGAAGGGCG UCGUCGCCCC GAGCGGUAGU AAGCAGGGAA CUCACCUCCA 60

AUUUCAGUAC UGAAAUUGUC GUAGCAGUUG ACUACUGUUA UGUGAUUGGU AGAGGCUAAG 120

UGACGGUAUU GGCGUAAGUC AGUAUUGCAG CACAGCACAA GCCCGCUUGC GAGAAU 176

(2) INFORMATION FOR SEQ ID NO: 10:

(i) SEQUENCE CHARACTERISTICS:
(A) LENGTH: 21 base pairs
(B) TYPE: nucleic acid
(C) STRANDEDNESS: single
(D) TOPOLOGY: linear (xi) SEQUENCE DESCRIPTION: SEQ ID NO: 10:

AAACAUGAGG AUUACCCAUG U 21

(2) INFORMATION FOR SEQ ID NO: 11:

(i) SEQUENCE CHARACTERISTICS:
(A) LENGTH: 21 base pairs
(B) TYPE: nucleic acid
(C) STRANDEDNESS: single
(D) TOPOLOGY: linear (xi) SEQUENCE DESCRIPTION: SEQ ID NO: 11:

CAACAUGAGG AAUACCCAUG U 21

(2) INFORMATION FOR SEQ ID NO: 12:

(i) SEQUENCE CHARACTERISTICS:
(A) LENGTH: 22 base pairs
(B) TYPE: nucleic acid
(C) STRANDEDNESS: single
(D) TOPOLOGY: linear (xi) SEQUENCE DESCRIPTION: SEQ ID NO: 12:

```
    AAACAUAAGG  AAAACCUAUG  UU                                                        2 2
```

( 2 ) INFORMATION FOR SEQ ID NO: 13:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 13:

```
    AUGCAUGUCU  AAGACAGCAU                                                            2 0
```

( 2 ) INFORMATION FOR SEQ ID NO: 14:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 14:

```
    GGGAGCCUCU  CAGAGGCGUU  AUUACC                                                    2 6
```

( 2 ) INFORMATION FOR SEQ ID NO: 15:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 15:

```
    CAGAUCUGAG  CCUGGGAGCU  CUCUGG                                                    2 6
```

( 2 ) INFORMATION FOR SEQ ID NO: 16:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 16:

```
    GAGAUACCAU  GAUCACGAAG  GUGGUUUUCC  C                                             3 1
```

( 2 ) INFORMATION FOR SEQ ID NO: 17:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 17:

```
    AAUCCUGCUC  AGUACGAGAG  GAACCGCAGG  UU                                            3 2
```

( 2 ) INFORMATION FOR SEQ ID NO: 18:

( i ) SEQUENCE CHARACTERISTICS:
        ( A ) LENGTH: 49 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 18:

```
    AACGGUUACA  CUCUCCCAUC  AAUCGUAAUG  GGUCUGAGGA  GUAAUCAUU                         4 9
```

( 2 ) INFORMATION FOR SEQ ID NO: 19:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 19:

```
GGUUUCCUGC  UUCAACAGUG  CUUGGACGGA  ACC                                    33
```

( 2 ) INFORMATION FOR SEQ ID NO: 20:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 20:

```
GACGAGCAUU  CCUAGGGGUC  UUUCCCUCU  CGCCAAAGGA  AUGCAAGGUC                  50
```

( 2 ) INFORMATION FOR SEQ ID NO: 21:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 21:

```
GACCGCAGGA  GUUUCGCAAG  AAACUUAAUC  CCCUGCGUAG                             40
```

( 2 ) INFORMATION FOR SEQ ID NO: 22:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 22:

```
GGUGGGCGCA  GCGUCAAUGA  CGCUGACGGU  ACA                                    33
```

( 2 ) INFORMATION FOR SEQ ID NO: 23:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 23:

```
GGUGGGCGCA  GCGUCAAUGA  CGCUGACGGU  ACACC                                  35
```

( 2 ) INFORMATION FOR SEQ ID NO: 24:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 24:

```
GGUGGGCGCA  GCUUCGGCUG  ACGGUACACC                                         30
```

( 2 ) INFORMATION FOR SEQ ID NO: 25:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 25:

CAGAUCUGAG CCUGGGAGCU CUCUGG        26

( 2 ) INFORMATION FOR SEQ ID NO: 26:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for any base.
            The letter "M"stands for A or C.

( x i ) SEQUENCE DESCRIPTION: SEQ ID NO: 26:

NNAUACCANN NNNNNNNCCU UGGMAGNN        28

( 2 ) INFORMATION FOR SEQ ID NO: 27:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 27:

UCCGGAUCGA AGUUAGUAGG CGGA        24

( 2 ) INFORMATION FOR SEQ ID NO: 28:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 28:

GAGCAUGCUG GUGCGGCUUU GGGCGCCGUG CUU        33

( 2 ) INFORMATION FOR SEQ ID NO: 29:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for any base.
            The letter "V"stands for guanosine,
            adenosine or cytidine.

( x i ) SEQUENCE DESCRIPTION: SEQ ID NO: 29:

NUGAUGVNCA UCCGN        15

( 2 ) INFORMATION FOR SEQ ID NO: 30:

( i ) SEQUENCE CHARACTERISTICS:
        ( A ) LENGTH: 10 base pairs
        ( B ) TYPE: nucleic acid
        ( C ) STRANDEDNESS: single (D) TOPOLOGY: linear (ix) FEATURE:
(D) OTHER INFORMATION: The letter "S" stands for guanosine
or cytidine.

(xi) SEQUENCE DESCRIPTION: SEQ ID NO: 30:

AAUGCCGASS                                                                                              10

(2) INFORMATION FOR SEQ ID NO: 31:

(i) SEQUENCE CHARACTERISTICS:
(A) LENGTH: 12 base pairs
(B) TYPE: nucleic acid
(C) STRANDEDNESS: single
(D) TOPOLOGY: linear (ix) FEATURE:
(D) OTHER INFORMATION: The letter "S" stands for guanosine
or cytidine.

(xi) SEQUENCE DESCRIPTION: SEQ ID NO: 31:

SSUUGAUGGG UU                                                                                           12

(2) INFORMATION FOR SEQ ID NO: 32:

(i) SEQUENCE CHARACTERISTICS:
(A) LENGTH: 25 base pairs
(B) TYPE: nucleic acid
(C) STRANDEDNESS: single
(D) TOPOLOGY: linear (ix) FEATURE:
(D) OTHER INFORMATION: The letter "R" stands for any purine.
The letter "D" stands for adenosine,
guanosine or uridine.
The letter "Y" stands for any pyrimidine.
The letter "H" stands for adenosine,
uridine or cytidine.

(xi) SEQUENCE DESCRIPTION: SEQ ID NO: 32:

RDGGGAACCU GCGUYUCGGC ACCHY                                                                             25

(2) INFORMATION FOR SEQ ID NO: 33:

(i) SEQUENCE CHARACTERISTICS:
(A) LENGTH: 19 base pairs
(B) TYPE: nucleic acid
(C) STRANDEDNESS: single
(D) TOPOLOGY: linear (ix) FEATURE:
(D) OTHER INFORMATION: The letter "H" stands for adenosine,
uridine or cytidine.
The letter "D" stands for adenosine,
guanosine or uridine.

(xi) SEQUENCE DESCRIPTION: SEQ ID NO: 33:

HHGGUUGAGU CUGUCCCDD                                                                                    19

(2) INFORMATION FOR SEQ ID NO: 34:

(i) SEQUENCE CHARACTERISTICS:
(A) LENGTH: 27 base pairs
(B) TYPE: nucleic acid
(C) STRANDEDNESS: single
(D) TOPOLOGY: linear (ix) FEATURE:
(D) OTHER INFORMATION: The letter "N" stands for any base.
The letter "R" stands for any purine.
The letter "S" stands for guanosine -continued or cytidine.

(xi) SEQUENCE DESCRIPTION: SEQ ID NO: 34:

NRUAGUUGGN NNCUNSUNNN CGCCGUN    27

(2) INFORMATION FOR SEQ ID NO: 35:

(i) SEQUENCE CHARACTERISTICS:
      (A) LENGTH: 32 base pairs
      (B) TYPE: nucleic acid
      (C) STRANDEDNESS: single
      (D) TOPOLOGY: linear (ix) FEATURE:
      (D) OTHER INFORMATION: The letter "R" stands for any purine.
         The letter "S" stands for guanosine
         or cytidine.
         The letter "K" stands for guanosine
         or uridine.
         The letter "M" stands for adenosine
         or cytidine.

(xi) SEQUENCE DESCRIPTION: SEQ ID NO: 35:

RSGGUUUCRU GUGKRGACUM UGCCGCGGCC SU    32

TABLE I

Characteristics of Ribozymes

Group I Introns

Size: ~200 to >1000 nucleotides.

Requires a U in the target sequence immediately 5' of the cleavage site.

Binds 4–6 nucleotides at 5' side of cleavage site.

Over 75 known members of this class. Found in *Tetrahymena thermophila* rRNA, fungal mitochondria, chloroplasts, phage T4, blue-green algae, and others.

RNAseP RNA (M1 RNA)

Size: ~290 to 400 nucleotides.

RNA portion of a ribonucleoprotein enzyme. Cleaves tRNA precursors to form mature tRNA.

Roughly 10 known members of this group all are bacterial in origin.

Hammerhead Ribozyme

Size: ~13 to 40 nucleotides.

Requires the target sequence UH immediately 5' of the cleavage site.

Binds a variable number nucleotides on both sides of the cleavage site.

Figure 1:
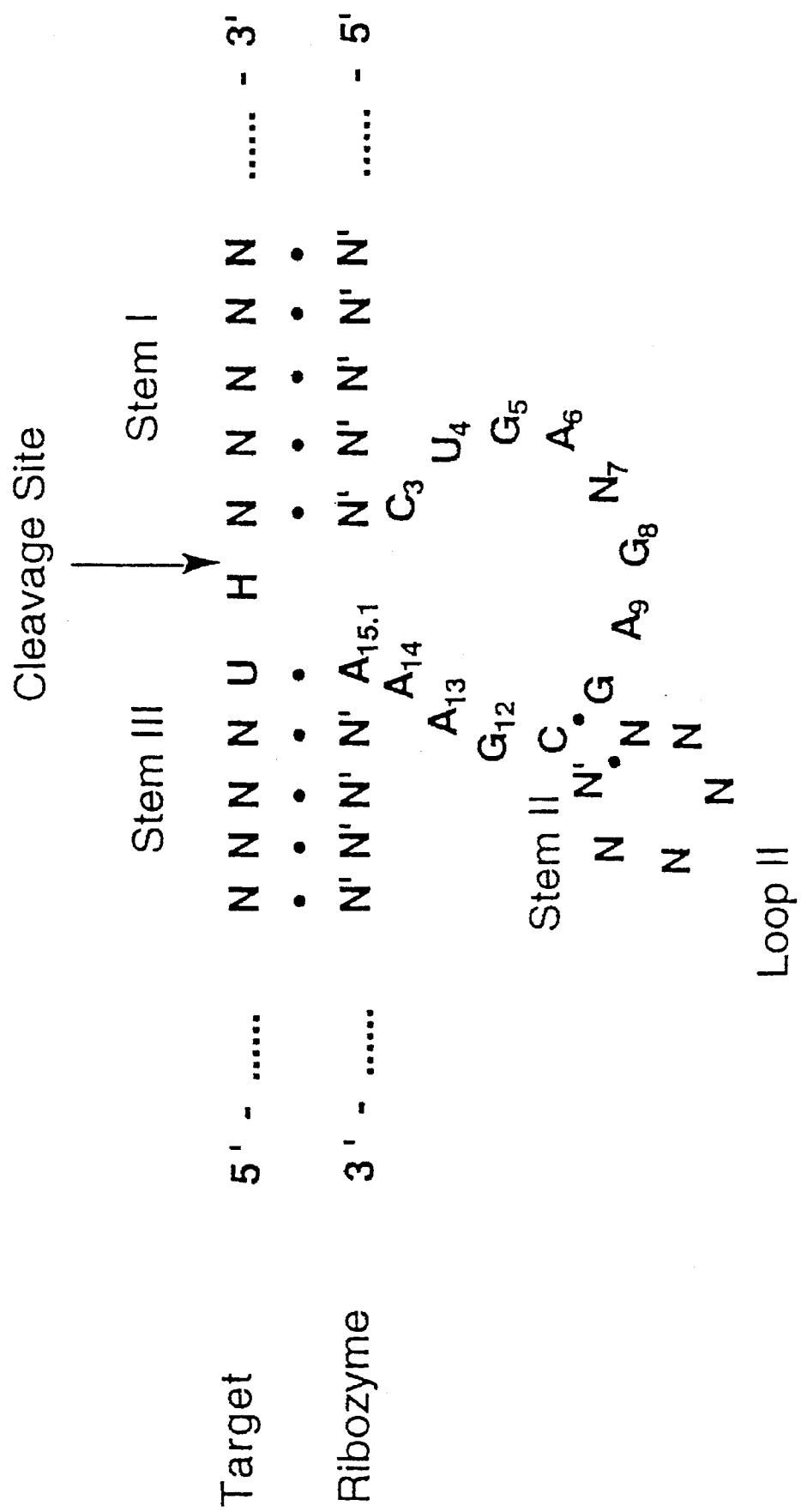

14 known members of this class. Found in a number of plant pathogens (virusoids) that use RNA as the infectious agent (FIG. 1)

Hairpin Ribozyme

Size: ~50 nucleotides.

Requires the target sequence GUC immediately 3' of the cleavage site.

Binds 4–6 nucleotides at 5' side of the cleavage site and a variable number to the 3' side of the cleavage site.

Figure 3:
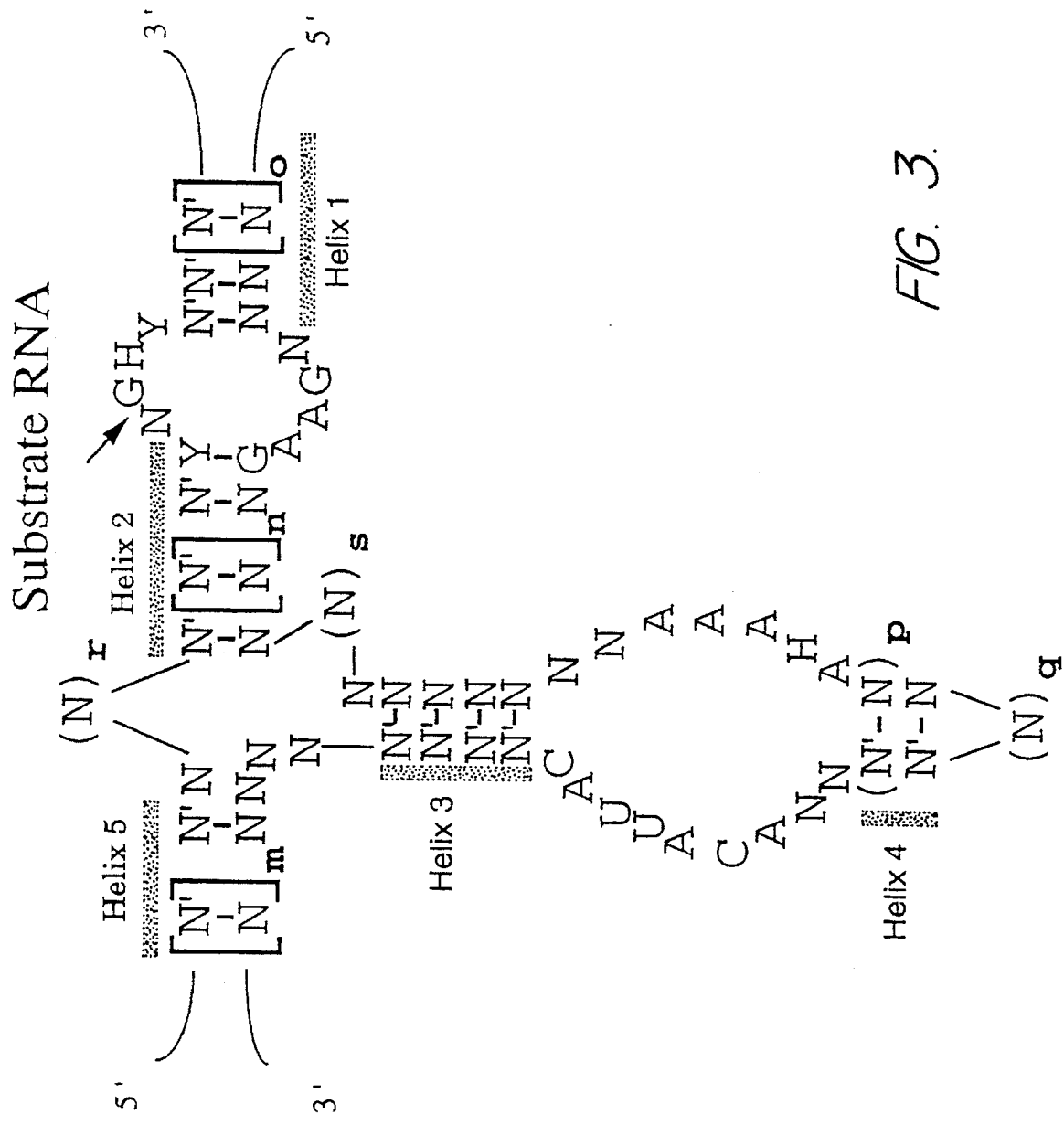

Only 3 known member of this class. Found in three plant pathogen (satellite RNAs of the tobacco ringspot virus, arabis mosaic virus and chicory yellow mottle virus) which uses RNA as the infectious agent (FIG. 3).

Hepatitis Delta Virus (HDV) Ribozyme

Size: 50–60 nucleotides (at present).

Cleavage of target RNAs recently demonstrated.

Sequence requirements not fully determined.

Binding sites and structural requirements not fully determined, although no sequences 5' of cleavage site are required.

Figure 4:
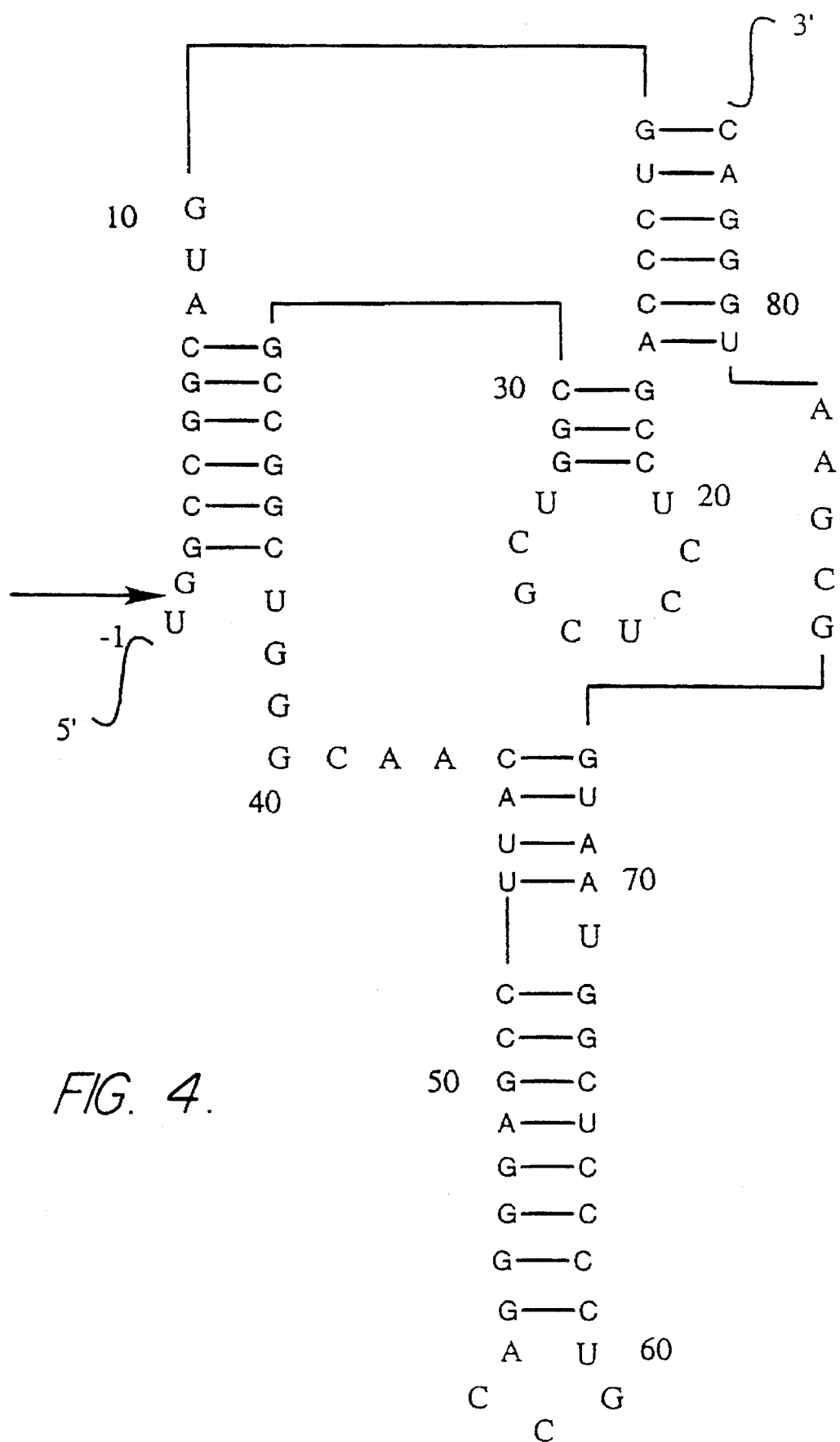
FIG. 4 is a representation of the general structure of the hepatitis delta virus ribozyme domain (SEQ ID No. 8) known in the art.

Only 1 known member of this class. Found in human HDV (FIG. 4).

Neurospora VS RNA Ribozyme

Size: ~144 nucleotides (at present)

Cleavage of target RNAs recently demonstrated.

Sequence requirements not fully determined.

Figure 5:
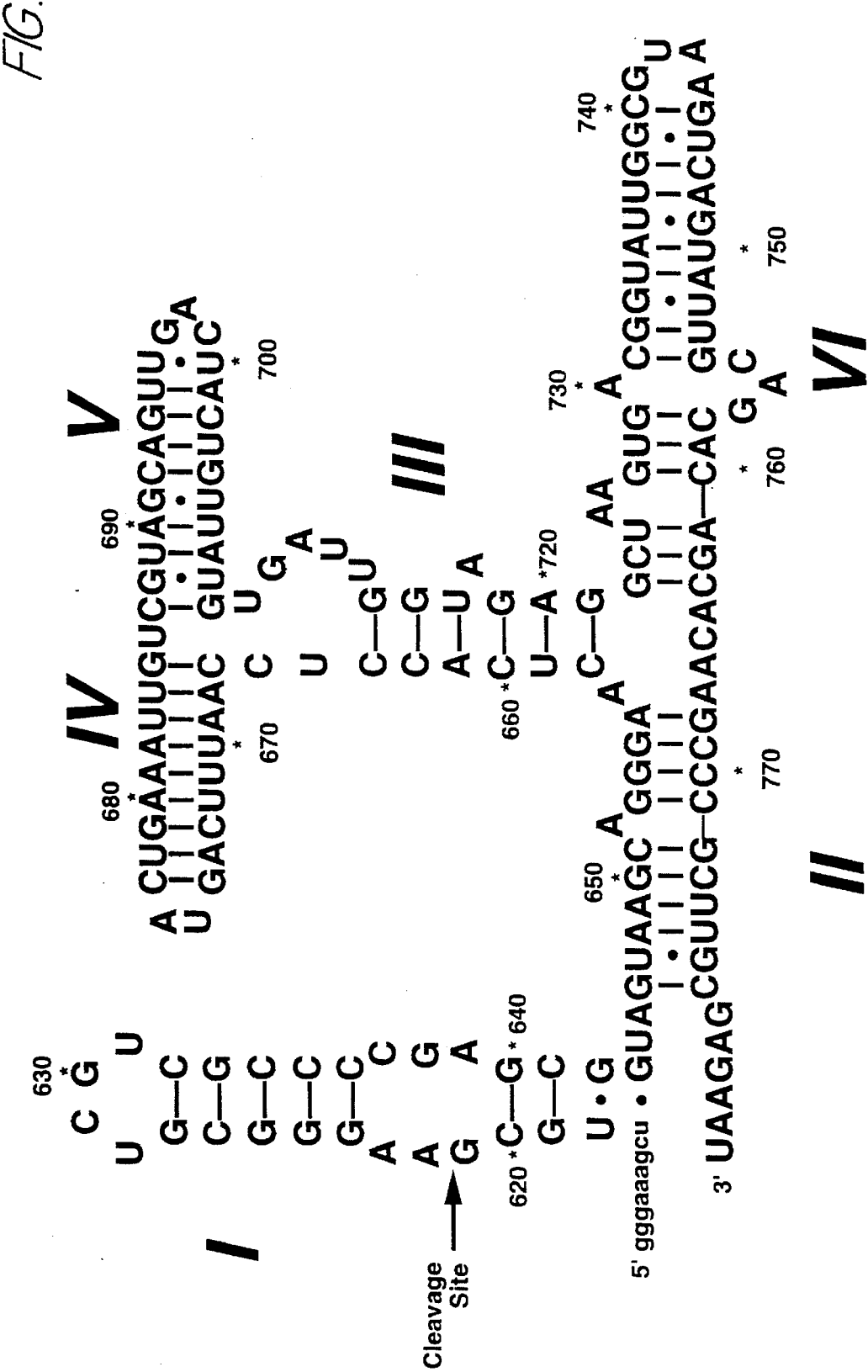
FIG. 5 is a representation of the general structure of the self-cleaving VS RNA domain (SEQ ID No. 9) known in the art.

Binding sites and structural requirements not fully determined. Only 1 known member of this class. Found in Neurospora VS RNA (FIG. 5).

TABLE 2

Kinetics of RNA Cleavage by the Hairpin Ribozyme (Hp) and the Hairpin Ribozyme with R17 Binding Site (HpR17)

| Reaction Conditions | Ribozyme | $k_{cat}/K_M$ (min$^{-1}$ · μM$^{-1}$) | $k_{cat}/K_M$ (rel$^c$.) |
|---|---|---|---|
| T.M.S$^a$, 37° C. | Hp | 3.1 | 1 |
|  | HpR17 | 5.6 | 1.8 |
| T.M.S, 25° C. | Hp | 2.1 | 0.7 |
|  | HpR17 | 4.6 | 1.5 |
| T.M.K$^b$, 25° C. | Hp | 1.2 | 0.4 |
|  | HpR17 | 2.7 | 0.9 |

$^a$T.M.S = 40 mM Tris.HCl, pH 7.5; 12 mM MgCl$_2$; 2 mM Spermidine
$^b$T.M.K = 40 mM Tris.Acetate, pH 7.5; 10 mM Mg.Acetate; 80 mM KCl
$^c$Relative $k_{cat}/K_M$; the second order rate constant is compared with the rate of Hp in T.M.S buffer at 237° C.

TABLE 3

Effect of R17 Protein Binding on RNA Cleavage Activity by the Hairpin Ribozyme

| Ribozyme | Presence of R17cp (0.5 µM) | $K_M$ (nM) | $k_{cat}$ (min$^{-1}$) | $k_{cat}/K_M$ (min$^{-1}$ · µM$^{-1}$) | $k_{cat}/K_M$ (rel.) |
|---|---|---|---|---|---|
| Hp | − | 62 ± 15 | 0.25 ± 0.02 | 4 | 1 |
| Hp | + | 67 ± 20 | 0.24 ± 0.03 | 3.6 | 1 |
| HpR17 | − | 51 ± 4 | 0.31 ± 0.005 | 6 | 1.7 |
| HpR17 | + | 58 ± 10 | 0.32 ± 0.02 | 5.7 | 1.7 |

We claim:

1. An enzymatic RNA molecule comprising: a protein binding site formed as a double-stranded RNA and a single-stranded loop, wherein said enzymatic RNA molecule is capable of specifically cleaving a separate RNA molecule, wherein said site is selected from a group shown in FIGS. 2 and 12–17 (SEQ. ID. Nos. 4, 10–16 and 18–28) inclusive, and wherein said enzymatic nucleic acid is in a hairpin motif.

2. The enzymatic RNA molecule of claim 1 or 4 wherein a protein is bound to said protein binding site in said enzymatic RNA molecule.

3. The enzymatic RNA molecule of claim 1 or 4 wherein the said protein binding site is adjacent to the 3' or the 5' end of said enzymatic RNA molecule.

4. An enzymatic RNA molecule comprising: a protein binding site formed as a double-stranded RNA and a single-stranded loop, wherein said enzymatic RNA molecule is capable of specifically ligating separate RNA molecules, wherein said site is selected from a group shown in FIGS. 2 and 12–17 (SEQ ID Nos. 4, 10–16 and 18–28) inclusive, and wherein said enzymatic nucleic acid is in a hairpin motif.

5. The enzymatic RNA molecule of claim 1 or 4, wherein said protein binding site is capable of binding R17 protein.

6. The enzymatic RNA molecule of claim 1 or 4, wherein said protein binding site is capable of binding human immunodeficiency virus encoded TAT protein.

7. The enzymatic RNA molecule of claim 1 or 4, wherein said protein binding site is capable of binding human immunodeficiency virus encoded Rev protein.

8. The enzymatic RNA molecule of claim 1 or 4, wherein said protein binding site is capable of binding mammalian iron response element binding protein.

9. The enzymatic RNA molecule of claim 1 or 4, wherein said protein binding site is capable of binding mammalian vascular endothelial growth factor.

10. A mammalian cell in vitro including the enzymatic RNA molecule of claim 1 or 4.

11. An expression vector comprising nucleic acid encoding the enzymatic RNA molecule of claim 1 or 4, in a manner which allows expression of that enzymatic RNA molecule within a cell in vitro.

12. A mammalian cell in vitro including an the expression vector of claim 11.

13. A method for increasing the activity of a an enzymatic RNA molecule in a hairpin motif by including a RNA protein binding site in the helix 4 region of said enzymatic RNA molecule.

14. A method for decreasing the activity of a hairpin ribozyme by including a RNA protein binding site in helix 4.

15. A method for localizing an enzymatic RNA molecule in a hairpin motif by providing a RNA protein binding sequence in said enzymatic RNA molecule and binding said site with a localizing protein.

* * * * *